United States Patent
Hoffman et al.

(10) Patent No.: US 7,101,713 B1
(45) Date of Patent: Sep. 5, 2006

(54) DNA TRANSFORMATION EFFICIENCY BY INHIBITING HOST CELL RESTRICTION

(75) Inventors: Leslie M. Hoffman, Madison, WI (US); Jerome J. Jendrisak, Madison, WI (US)

(73) Assignee: Epicentre Technologies Corporation, Madison, WI (US)

( * ) Notice: Subject to any disclaimer, the term of this patent is extended or adjusted under 35 U.S.C. 154(b) by 0 days.

(21) Appl. No.: 10/147,564

(22) Filed: May 16, 2002

(51) Int. Cl.
*C12N 15/64* (2006.01)

(52) U.S. Cl. ............... 435/473; 435/474; 435/476
(58) Field of Classification Search ........... 435/471, 435/472, 473, 475, 476, 477, 478, 479, 483, 435/484, 485, 486, 487, 488; 530/300, 350
See application file for complete search history.

(56) References Cited

U.S. PATENT DOCUMENTS 4,910,140 A * 3/1990 Dower .................. 435/488
6,294,385 B1 * 9/2001 Goryshin et al. ........... 435/455

OTHER PUBLICATIONS

Reuter et al., Zeitschrift Fur All gemeine Mikrobiologie 20 (5): 345-354, 1980.*
Krueger et al., Mol. Gen. Genet. 185: 457-461, 1982.*
Mark et al., J. Biol. Chem. 256: 2573-2578, 1981.*

* cited by examiner

*Primary Examiner*—Nancy Vogel
(74) *Attorney, Agent, or Firm*—Quarles & Brady LLP

(57) ABSTRACT

It can be difficult to achieve efficient transformation of many strains of bacterial cells due in part to the presence of one or more restriction and modification (R-M) systems in the cells that restricts unmodified transforming DNA. Phage T7 OCR protein is a potent inhibitor of Type I R-M systems. Methods are disclosed for improving transformation efficiency of Eubacterial and Archaebacterial cells having an R-M system by introducing into the cells an inhibitor of the restriction activity. For example, addition of 1–5 micrograms of T7 OCR protein to 50 microliters of electrocompetent cells having a Type I R-M system prior to electroporation significantly increased transformation efficiency by unmodified plasmids, fosmid clones, and artificial transposons comprising synaptic complexes. Other inhibitors or restriction activity, such as phage-encoded proteins and proteins encoded by conjugative plasmids, as well as other disclosed inhibitors, also can be used to improve transformation (and transposition) efficiency. Host cells with heritable improved transformation efficiency can be made by transforming a cell having an R-M system with an expressible gene which encodes an inhibitor of the restriction activity, which gene can be conditionally expressible. Transient expression of a gene on an unmodified transforming DNA can also be improved by in vivo inhibition of restriction in host cells having an R-M system. Kits and compositions for carrying out the methods of the invention and host cells made using the methods are also disclosed.

7 Claims, No Drawings

DNA TRANSFORMATION EFFICIENCY BY INHIBITING HOST CELL RESTRICTION

BACKGROUND OF THE INVENTION

1. Field of the Invention

This invention relates to methods and compositions for improving DNA transformation efficiency of host strains by inhibiting host cell restriction activity.

2. Prior Art

DNA transformation is an important process in molecular biology. Transformation is the process of contacting a cell with a DNA molecule under conditions so that the DNA is taken up and incorporated into the cell so has to produce a heritable genotype. The cell into which the DNA is introduced is commonly referred to a "host cell." Host cells used for DNA transformation include, but are not limited to, bacterial cells. A host cell can be a cell comprising any organism. Many aspects of transformation, including some methods and information for different types of host cells, have been described in a review [Smith, H. O., et al., "Genetic Transformation," In: *Ann. Rev. Biochem.*, 50: 41–68, 1981), incorporated herein by reference.

One purpose for transformation, the process of which is also referred to as "transforming a host cell," is to clone a DNA molecule comprising natural or synthetic DNA. In order to clone a DNA molecule, the DNA is joined to a replicable vector, such as a plasmid or bacteriophage vector, which is capable of replicating autonomously in the host cell. Once the DNA is joined to the vector, the resulting "recombinant DNA" is used to transform a suitable host cell. Then the host cell is grown in a culture medium in order to multiply the number of cells, which are descendents of the host cell, each of which contains one or more copies of the recombinant DNA. This process of "DNA cloning" or "molecular cloning" thus enables one to obtain multiple copies of a single recombinant DNA molecule. Many cloning vectors and methods related to cloning and transformation are described or cited by Joseph Sambrook and David W. Russell [*Molecular Cloning—A Laboratory Manual Volumes* 1–3, Third Edition, Cold Spring Harbor Laboratory Press, Cold Spring Harbor, N.Y., 2001], incorporated herein by reference.

To maintain the plasmid vector in the cell, the vector DNA typically contains a selectable marker. Any selectable marker known in the art can be used. For an *E. coli* vector, any gene that conveys resistance to any antibiotic effective in the cell, or any gene that conveys a readily identifiable or selectable phenotypic change can be used. Preferably, antibiotic-resistance markers, including, but not limited to, genes that confer resistance to kanamycin or other aminoglycoside antibiotics such as dihydrostreptomycin, gentamycin, neomycin, paromycin, or streptomycin, or to amphenicols, such as chloramphenicol (for which the gene is known as chloramphenicol transacetylase or CAT), are used. Those with skill in the art will know or know how to find other antibiotic-resistance genes and non-antibiotic selection methods to select for maintenance of a plasmid or other vector. A host cell can also be transformed by natural or synthetic DNA which is not joined to (or "cloned in") a replicable vector. For example, it is known in the art that if at least a portion of the transforming DNA has homology with DNA in the host cell, the transforming DNA can be incorporated into a host cell that has a "homologous recombination system" [e.g.s, See: Camerini, R. D., and Hsieh, P., "Homologous recombination proteins in prokaryotes and eukaryotes," *Annual Rev. Genetics*, 29: 509–552, 1995; Kowalczykowski, S. C., et al., "Biochemistry of homologous recombination in *Escherichia coli*," *Microbiol. Rev.*, 58: 401–465, 1994; Heyer, W. D., and Kohli, J., "Homologous recombination," *Experientia*, 50: 189–191, 1994; Smith, G. R., "Homologous recombination in prokaryotes," *Microbiol. Rev.*, 52: 1–28, 1988]. A homologous recombination system is comprised of enzymes which catalyze various reactions so as to bring about incorporation of foreign DNA which has at least some homology to DNA in the host cell into the DNA of the host cell.

Recently, researchers demonstrated that a host cell also can be transformed with a synaptic complex consisting of a DNA molecule comprising an artificial transposon and a transposase enzyme which recognizes the ends of the transposon [Goryshin and Reznikoff, U.S. Pat. No. 6,294,385]. Following transformation of the host cell with the synaptic complex, the transposase in the complex is activated by intracellular magnesium ions in the host cell so as to catalyze transposition of the transposon into the cellular DNA of the transformed host cell. In this case, the transforming DNA is introduced into the host cell's DNA and therefore, the transforming DNA does not require the capability for autonomous replication in the host cell.

A variety of methods and conditions are known in the art for improving the efficiency of transformation of a given host cell. These methods and conditions vary for different organisms and even for different strains of a particular organism. The efficiency of transformation is usually measured by stating the number of independently-transformed host cells that are obtained using a certain quantity of a transforming DNA under defined conditions of transformation. In most cases in which the transformation efficiency is determined, the transforming DNA encodes at least one gene, such as an antibiotic resistance gene, which can be used as a selectable marker. It is commonly stated in the art, for example, that $10^2$ up to about $10^{10}$ colony forming units (cfu) of a transformed *Escherichia coli* host strain (which is resistant to the antibiotic in the medium because of the presence of the antibiotic-resistance gene in the transforming DNA) are obtained per microgram of transforming DNA under the specified conditions, which would be described. In most experiments in which the transformation efficiency is determined using transforming DNA that encodes an antibiotic resistance gene, equal quantities of host cells which have been treated with transforming DNA are plated on two different media; one medium contains the antibiotic for which the transforming DNA encodes resistance and the other medium does not contain this antibiotic. Thus, the number of colonies which grow on the antibiotic-containing medium is used to calculate the cfu per quantity of transforming DNA under the conditions used, and the number of cfu on the antibiotic-containing plates divided by the number of cfu on the medium without antibiotic indicates the relative proportion of the host cells that were transformed by the transforming DNA.

One method to increase the uptake of a DNA molecule, or the efficiency of transformation, is to treat the host cell so as to increase its ability (or "competence") to take up DNA under transformation conditions. For example, treatment of bacterial cells with calcium chloride increases the cells' ability to take up DNA (Mandel, M. and Higa, A., "Calcium-dependent bacteriphage DNA infection," *J. Mol. Biol.*, 53: 159–162, 1970; Cohen, S. N. et al., "Construction of biologically functional bacterial plasmids in vitro," *Proc. Natl. Acad. Sci. USA*, 73: 3240–3244, 1973). Many other variations have been described for increasing the competence of the cells by treating them with chemicals (e.g., Hanahan, D.

"Studies on transformation of *Escherichia coli* with plasmids," *Gene*, 24: 317–326, 1983; Hanahan, D., et al., "Plasmid transformation of *E. coli* and other bacteria," *Methods, Enzymol.* 204: 63–113, 1991). This process is commonly referred to in the art as "making the cells chemically competent". Alternatively, a preferred method of transformation employs pulses of electric current to introduce the DNA into host cells, a process referred to as electroporation. The cells used for electroporation are usually grown and treated so as to make them more capable of transformation by electroporation and such cells are referred to in the art as "electrocompetent cells". Electroporation of prokaryotic cells with DNA material is typically achieved by the subjecting host cells with high-intensity electric pulses to make the cell walls "porous", as described by U.S. Pat. No. 4,910,140. Other methods for transformation of host cells are known by those with skill in the art, such as, but not limited to, introducing transforming DNA into the host cells by means of microinjection. or by encapsidation in a bacteriophage or viral coat, or in a liposome.

Transformation of various types of cells, including different strains of bacterial cells, can be difficult to achieve or very inefficient. The various factors that influence the efficiency of transformation are poorly understood. In order to study and manipulate various types of cells, it is therefore critical to find methods to increase the efficiency of DNA transformation of these cells.

The presence of a restriction and modification system ("R-M system") in a host cell is well known in the art to be an important factor in preventing or reducing the efficiency of transformation by transforming DNA that is unmodified with respect to the R-M system in the host cell. Type I, Type II, and Type III R-M systems are described and discussed and citations are given in review articles by Noreen E. Murray ["Type I Restriction Systems: Sophisticated Molecular Machines (a Legacy of Bertany and Weigle)." *Microbiol. Molec. Biol. Rev.*, 64: 412–434, 2000; "Immigration control of DNA in bacteria: self versus non-self," *Microbiology*, 148: 3–20, 2002] and Robert Yuan ["Structure and Mechanism of Multifunctional Restriction Endonucleases," *Ann. Rev. Biochem.*, 50: 285–315, 1981], and in the $3^{rd}$ edition of Sambrook and Russell's *Molecular Cloning—A Laboratory Manual*, all of which are incorporated herein by reference. Thus, as discussed by Murray [op cif], the DNA in a prokaryotic host cell that has an R-M system is modified so that the cell's own DNA is protected from digestion (or "restriction") by an endonuclease (also referred to as a "restriction enzyme") that is present in the cell, but transforming DNA from another cell which lacks the modification system is not protected from digestion by the endonuclease (if the transforming DNA has one or more sequences which are recognized by the endonuclease as sites for digestion by the endonuclease). The modification enzymes that protect the DNA from digestion are generally DNA methyltransferases which catalyze methylation of specific nucleic acid bases within the target sequence that is digested by the endonuclease. Thus, the modification enzymes block endonuclease digestion of the methylated (or "modified") DNA. As stated by Murray [*Microbiol. Molec. Biol. Rev.*, 64: p. 413, 2000], "Classically, a restriction enzyme is accompanied by it's cognate modification enzyme, and the two comprise a restriction and modification (R-M) system. Most restriction systems conform to this classical pattern. There are, however, some restriction endonucleases that attack DNA only when their target sequence is modified; such modification-dependent restriction enzymes do not, therefore, coexist with a cognate modification enzyme . . . The classical R-M systems and the modification-dependent restriction enzymes share the potential to attack DNA derived from different strains and thereby restrict DNA transfer."

DNA which lacks methyl groups or other modifications which block digestion by the restriction activity portion of an R-M system is referred to as "unmodified" DNA with respect to that R-M system. Unmodified DNA molecules introduced into host cells are often attacked by R-M systems that recognize specific sequences in the DNA and rapidly cleave the DNA into fragments. For example, Type I R-M enzymes are thought to exist in a high percentage of Eubacteria and Archaebacteria, and pose a barrier for entry and establishment of foreign DNA [Murray, N. E., ibid; and Titherage, A. J. B., et al., *Nucl. Acids Res.*, 29: 4195–4205, 2001]. There are many situations in which the modification state of transforming DNA leads to restriction in the recipient host cell [Ando, T. et al., *Molec. Microbiol.*, 37: 1052–1065, 2000]. It would be highly desirable to improve transformation efficiency of such strains having R-M systems.

Many R-M systems are encoded by multiple genes. By way of example, but not of limitation, Type I R-M systems are generally encoded by three genes hsdR, hsdM, and hsdS—which encode three protein subunits, colloquially referred to as "R" (for "restriction"), "M" (for "modification"), and "S" (for "specificity"). These subunits can exist in two kinds of functional complexes in bacteria. An R-M complex with all three subunits (R.sub.2., M.sub.2., S.sub.1.) comprises an R-M system. Another complex, which has only methyltransferase activity and no restriction activity, comprises only two kinds of subunits (M.sub.2., S.sub.1.) and lacks R subunits [See: Murray, N. E., *Microbiology*, 148: 3–20, 2002]. Type III R-M system have similarities to Type I systems with respect to their molecular structure and other characteristics, whereas Type II R-M systems have separate restriction enzymes (which are the common commercial enzymes used in molecular biology) and methyltransferase modification enzymes [ibid].

Because R-M systems present a barrier to transformation of unmodified DNA, special bacterial strains have been developed for a limited number of organisms which are devoid of the known R-M systems for use in cloning and other applications in which unmodified DNA is used for transformation. Such strains are commonly referred to in the art as being "restriction minus" and the specific genotype of a strain is often presented so as to indicate which R-M system has been deleted or inactivated by mutation in the strain. These restriction minus strains are used as host cells because they do not digest or restrict the unmodified transforming DNA that enters the cells during transformation. By way of example, but not of limitation, an electrocompetent form of an *E. coli* strain for use in cloning when electroporation is used for transformation is commercially available under the trademarked name of *E. coli* TransforMax.sup.TM. EC100.sup.TM. (EPICENTRE); this strain is restriction minus and the genotype with respect to the R-M systems is described as "mcrA delta(mrr—hsdRMS—mcrBC)." Since *E. coli* strain TransforMax.sup.TM. EC10.sup.TM. is restriction minus, and also because the cells have been prepared so as to maximize the electrocompetence of the cell, very high transformation efficiencies are obtained when unmodified transforming DNA is used to transform the cells by electroporation. On the other hand, if unmodified DNA molecules, including, for example, plasmids or other replicons, or transposons, are taken from non-modifying cells or prepared synthetically or by PCR or by other means, and then used to transform competent cells which have an R-M system, such as, for example, cells having a Type I R-M system, the transformation will either be impossible or the transformation efficiency will be greatly reduced. Since it is highly desirable to be able to study and to be able to transform many cells which have an R-M system, including many pathogens and other strains of medical or commercial interest, there is a great need in the art to develop methods for improving transformation of such cells with unmodified DNA. It is therefore highly desirable in the art to find methods to overcome the barrier to transformation of host cells which have an R-M system which digests unmodified transforming DNA.

Many examples are known in which the R-M system barrier to transformation by unmodified phage and conjugative plasmid DNA is overcome by natural means. By way of example, but not of limitation, bacteriophages T7 and T3, which infect enteric bacterial cells, have evolved natural mechanisms to defeat host R-M systems. These bacteriophages produce a polypeptide encoded by the 0.3 ocr gene early in infection, before the remainder of the phage genome is internalized in the host cell, that mimics a DNA molecule; this polypeptide binds to the R-M system and prevents it from binding to DNA substrates, thereby inhibiting restriction activity of the R-M system [Bandyopadhhay, P. K., et al., *J. Mol. Biol.*, 182: 567–578, 1985]. It has been shown that this polypeptide, referred to as "Overcomes Classical Restriction" or "OCR," has a conformation resembling the bent structure of unmodified DNA when it binds to Type I R-M complexes, and that OCR binds the restriction complexes tightly [Atanasiu, O., et al., *Nucl. Acids Res.*, 29: 3059–3068,12, 2001 and Walkinshaw, M. D., et al., *Molec. Cell*, 9: 187–194, 2002]. Thus, by acting as a molecular "decoy", OCR protein inhibits restriction and prevents destruction of entering bacteriophage DNA.

In addition to phage-encoded inhibitors of restriction activity like the OCR proteins, inhibitors of the restriction activity of R-M systems have also been identified in bacteria which contain naturally-occurring transmissible plasmids, meaning plasmids which can be transferred from one bacterial strain to another by conjugation. By way of example, but not of limitation, it has been reported that certain transmissible plasmids have genes designated ardA, or ardB, or ardC that encode polypeptides called "Ard" for "alleviation of restriction of DNA" which provide general protection against restriction by all Type I R-M systems [Belogurov, A. A., et al, "IncN plamid pKM101 and Incl1 plasmid Col1b-P9 encode homologous anti-restriction proteins in their leading regions," *J. Bacteriol.*, 174: 5079–5085, 1992; Belogurov, A. A., et al., "Plasmid pKM101 encodes two non-homologous anti-restriction proteins (ArdA and ArdB) whose expression is controlled by homologous regulatory sequences," *J. Bacteriol.*, 175: 4843–4850, 1993; Belogurov, A. A., et al., "Antirestriction protein Ard (Type C) encoded by IncW plasmid pSa has a high similarity to the 'protein transport' domain of TraC1 primase of promiscuous plasmid RP4," *J. Mol. Biol.*, 296: 969–977, 2000]. Belogurov et al. reported that, in addition to inhibiting Type I R-M systems, ArdA also inhibits the Type II enzyme EcoRI. Recently, it was reported that, as with T3- and T7-encoded OCR Protein, the ard gene is in the leading edge of the DNA that is transferred into the host cell during conjugation, and, by a using special promoters within secondary structures of single-stranded DNA, it is transcribed into Ard protein prior to entrance of the remaining plasmid DNA into the host cell [Althorpe, N. J., et al., "Transient transcriptional activation of the Incl1 plasmid anti-restriction gene (ardA) and SOS inhibition gene (psiB) early in conjugation," *Mol. Microbiol.* 31: 133–142, 1999; Bates, S. R., et al., "Expression of leading region genes on Incl1 plasmid Col1b-P9: genetic evidence for single-stranded DNA transcription," *Microbiology*, 145: 2655–2662, 1999]. It has been proposed that Ard Proteins alleviate restriction of DNA by mimicking the sequences of the specificity ("S") subunits of Type I R-M systems and displace this S subunit from the R-M complex [Belogurov, A. A., and Delver, E. P., "A motif conserved among the type I restriction-modification enzymes and anti-restriction proteins: a possible basis for mechanism of action fo plasmid-encoded antirestriction functions," *Nucleic Acids Res.*, 23: 785–787, 1995], but it is also possible that the mechanism is similar to that of OCR Protein.

Other natural mechanisms by which unmodified forms of phages, plasmids and at least one conjugative transposon avoid restriction in host cells having an R-M system in which they would otherwise be degraded are described, discussed and referenced [Murray, N. E., *Microbiol. Molec. Biol. Rev.*, 64: 412–434, 2000 (especially the section entitled "Mechanisms by Which Plasmids and Phages Avoid Restriction" on pp. 425–426); Bickle, T. A. and Kruger, D. H., "Biology of DNA restriction," *Microbiol. Rev.* 57: 434–450, 1993; and Kruger, D. H. and Bickle, T. A. "Bacteriophage survival: multiple mechanisms for avoiding the deoxyribonucleic acid restriction systems of their hosts," *Microbiol. Rev.* 47: 345–360,1983], all of which are incorporated herein by reference.

Although it is known in the art that one can increase the transformation efficiency of transforming DNA for a host cell having an R-M system by modifying the restriction sites on the transforming DNA prior to transformation, this is not practical in many cases. For example, one might not know what restriction sites are present on the DNA, what sites on the DNA must be modified to protect it, or how to achieve the desired modification. Also, although some of the R-M systems that are present in a number of *E. coli* strains have been identified, this is not the case for many other strains of *E. coli* and definitely is not the case for most other strains of eubacteria and archaebacteria. Noreen Murray has discussed the detection, distribution and diversity of R-M systems [*Microbiol. Molec. Biol. Rev.*, 64: 412–434, 2000 (especially, see pp. 426–430)], incorporated herein by reference. As discussed therein, at least about half of the bacteria in a sequence database had genes that appeared to be Type I-specific R-M genes. More than 1% of the small genome of the medically important bacterium *Helicobacter pylori* encoded R-M systems, three of which were Type I [Tomb, J. F., et al., "The complete genome sequence of the gastric pathogen *Helicobacter pylori*," *Nature*, 388: 539–547, 1997]. It would be difficult to overcome the complex R-M systems of *H. pylori* by modifying a transforming DNA in order to avoid its restriction by such a host cell. The R-M systems present in most other bacteria of medical, commercial and food importance are not yet defined. Even more challenging is the fact that the actual restriction sites on the DNA of Type I and Type III R-M systems are very difficult to define and identify even after the presence of a R-M system has been shown to be present by screening for R-M genes. Further, the modification enzymes comprising R-M systems from many organisms have not been purified, making it difficult to modify transforming DNA using in vitro treatment with modifying enzymes.

It would be highly desirable to be able to increase the transformation efficiency of many host cells in which the R-M systems have not yet been defined, even if the sequence of the transforming DNA is not known. The present invention provides new and powerful methods for achieving transformation and increasing the transformation efficiency by unmodified DNA for many host cells having an R-M system. These methods do not require prior knowledge of the restriction sites on the unmodified transforming DNA or the restriction specificity of the R-M system. They can be used to increase transformation efficiency of a variety of host cells having R-M systems which restrict unmodified transforming DNA at different sites. The present invention also provides methods for genetically modifying host cells which have an R-M system so they can be transformed by unmodified transforming DNA with higher efficiency. The invention also discloses kits and compositions for carrying out the methods of the invention, or which are made using these methods.

OBJECTS OF THE INVENTION

It is currently very difficult or impossible to transform cells of many organisms with unmodified DNA, and even when transformation is possible for a particular kind of cell, the efficiency is usually very low. It is an object of the invention to provide a method for improving transformation efficiency of host cells having a restriction and modification (R-M) system with an unmodified transforming DNA by introducing into the host cell an inhibitor of the restriction activity of the host cell's R-M system so as to reduce or block restriction of the unmodified transforming DNA during transformation. A preferred object of the invention is to provide methods to improve transformation efficiency of host cells selected from among Eubacteria or Archaebacteria. Another preferred object of the invention is to provide methods to improve transformation efficiency of Eubacterial and Archaebacterial host cells having at least one R-M system selected from among a Type I R-M system, a Type II R-M system, or a Type III R-M system by unmodified transforming DNA that has at least one site which, in the absence of an inhibitor for the restriction activity of the host cell, would be restricted in the host cell.

A primary object of the invention is to provide methods to improve transformation efficiency of host cells by unmodified DNA by introducing into the host cells a composition or compositions that bind to a site on an enzyme of the host cells' R-M system so as to reduce or block restriction of unmodified transforming DNA during transformation. Most preferably, the composition will inhibit the restriction activity of a broad range of Eubacterial and Archaebacterial cells.

Since electroporation is the most efficient method for transforming some kinds of Eubacterial or Archaebacterial cells, an especially preferred object of the invention is to provide methods for improving transformation efficiency of host cells with unmodified transforming DNA by electroporation, wherein a composition that binds to a site on an enzyme of the host cells' R-M system is introduced into the host cells during the process of electroporation so as to reduce or block restriction of the unmodified transforming DNA.

It is an object of this invention to improve the stability of foreign genetic material delivered into host cells in molecular cloning and recombinant DNA applications. A preferred object of the invention is to improve transformation efficiency of a host cell having an R-M system with unmodified transforming DNA comprising vector DNA. Another preferred object of the invention is to improve transformation efficiency of a host cell having an R-M system with unmodified transforming DNA comprising a polynucleotide selected from the group comprising plasmids, suicide plasmids, shuttle vectors, cosmids, fosmids, replicons, amplicons, BACs, YACs, and episomes of all types, or mixtures thereof.

Another preferred object of the invention is to improve transformation efficiency of a host cell having an R-M system with unmodified transforming DNA comprising a transposon or an artificial transposon. Still another preferred object of the invention is to improve transformation efficiency of a host cell having an R-M system with unmodified transforming DNA comprising a synaptic complex between an artificial transposon and a transposase, which synaptic complex, upon introduction into the host cell, is capable of catalyzing in vivo transposition of the transposon into DNA present in the host cell.

It is an object of the invention to improve transformation efficiency of a host cell having an R-M system with unmodified transforming DNA comprising a DNA polynucleotide, at least a portion of which has homology to DNA present in the host cell. A preferred object of the invention is to improve transformation efficiency of a host cell having an R-M system with unmodified transforming DNA comprising a PCR amplification product or a synthetic oligonucleotide, at least a portion of which has homology to DNA in the host cell. Another preferred object of the invention is to improve transformation efficiency of a host cell having an R-M system with unmodified transforming DNA wherein the unmodified transforming DNA, upon introduction into the host cell, undergoes homologous recombination with DNA present in the host cell.

It is another object of the invention to obtain transformed cells which result from use of the methods for improving transformation efficiency of the host cells. By way of example, but not of limitation, one object of the invention is to obtain transformed cells having new heritable genotypes and new properties which have commercial applications. Still another object is to obtain transformed cells that contain genes which are capable of expressing proteins that are useful for some commercial purpose using methods of the invention which permit improved transformation of a host cell. One object of this aspect of the invention is to improve transformation efficiency with unmodified transforming DNA of a host cell comprising a lactic acid bacterium having an R-M system.

Another object of the invention is to provide a kit for improving transformation efficiency with unmodified transforming DNA of host cells having an R-M system. A preferred object of the invention is to provide kits for improving transformation efficiency, wherein the kits comprise an inhibitor of the restriction activity of an R-M system of the host cells. A preferred object of the invention is to provide a kit for improving transformation efficiency of a host cell having an R-M system with unmodified transforming DNA, wherein the kit comprises a preparation of an inhibitor which binds to the host cell's R-M system so as to reduce or block restriction of unmodified transforming DNA during transformation and which kit is for use with transforming DNA that is introduced into the host cell by electroporation.

Still other objects of the invention are to provide increased transformation efficiencies of DNA comprising plasmids, fosmids, cosmids, BACs and transposons in bacterial strains having an R-M system selected from among a Type I R-M system, a Type II R-M system, and a Type III R-M system.

It is another object of the invention to provide a protein that inhibits the R-M system of the host cells in vivo during genetic transformation.

Yet another object of the invention is to provide conditions in which unmodified foreign nucleic acids are protected from restriction damage in the host cells during genetic transformation.

Another object of the invention is to provide optimized systems for introduction of active undamaged transposon synaptic complexes comprising unmodified artificial transposons into host cells in order to obtain higher transposition efficiencies in vivo.

Yet another object of the invention is to provide conditions in which unmodified foreign nucleic acids are protected from restriction damage following introduction into host cells in order to obtain transient gene expression of genes on the unmodified foreign DNA.

Yet another object of the invention is to provide a kit for obtaining improved transient expression of genes on unmodified foreign DNA which is introduced into host cells by electroporation, wherein the kit comprises a preparation of an inhibitor of the restriction activity of an R-M system present in the host cells.

A different preferred object of the invention is to provide a method for genetically modifying a cell having an R-M system in order to obtain a host cell having a heritable genotype which encodes a phenotype which permits improved transformation efficiency by unmodified transforming DNA.

One object of the invention is to obtain host cells having a heritable genotype which encodes a phenotype that permits improved transformation efficiency by unmodified transforming DNA for host cells selected from the group consisting of Eubacteria or Archaebacteria. A preferred object is to obtain host cells which have which have a heritable genotype which encodes a phenotype that permits improved transformation efficiency by unmodified transforming DNA and which can be used for commercial applications. Without limiting the invention, one example of this object of the invention is to obtain lactic acid-producing bacteria which have improved transformation efficiency by unmodified transforming DNA.

Another object of this aspect method of the invention is to obtain host cells having a heritable genotype which encodes a phenotype comprising improved transformation efficiency by unmodified transforming DNA for host cells having at least one restriction and modification (R-M) system selected from among a Type I R-M system, a Type II R-M system, or a Type III R-M system.

Another object is to obtain host cells having a heritable genotype which encodes a phenotype comprising improved transformation efficiency by unmodified transforming DNA which is introduced into the host cells by electroporation.

Another object is to obtain host cells having a heritable genotype which encodes a phenotype comprising improved transformation efficiency by unmodified transforming DNA comprising a transposon or an artificial transposon. A preferred object of this aspect of the invention is to obtain host cells having a heritable genotype which encodes a phenotype comprising improved transformation efficiency by unmodified transforming DNA comprising a transposon or an artificial transposon that comprises a synaptic complex between the transposon and a transposase.

Another object is to obtain host cells having a heritable genotype which encodes a phenotype comprising improved transformation efficiency by unmodified transforming DNA comprising a polynucleotide selected from the group comprising plasmids, suicide plasmids, shuttle vectors, cosmids, fosmids, oligonucleotides, replicons, amplicons, BACs, YACs, episomes of all types, or mixtures thereof.

Another object is to obtain host cells having a heritable genotype which encodes a phenotype comprising improved transformation efficiency by unmodified transforming DNA comprising a polynucleotide, at least a portion of which has homology to DNA present in the host cell.

Yet another preferred object of the invention is to provide kits for genetically modifying cells having an R-M system in order to obtain a host cells having a heritable genotype which encodes a phenotype that permits improved transformation efficiency by unmodified transforming DNA.

DETAILED DESCRIPTION OF THE INVENTION

A preferred embodiment of the invention is a method for improving transformation efficiency of host cells having a restriction and modification (R-M) system with an unmodified transforming DNA, said method comprising introducing into the host cell an inhibitor of the restriction activity of the host cell's R-M system so as to reduce or block restriction of the unmodified transforming DNA during transformation.

Host cells of the Invention

Preferred host cells of the invention are host cells selected from among Eubacteria and Archaebacteria. Any host cells having an R-M system which has restriction activity that reduces transformation efficiency of unmodified transforming DNA and for which an inhibitor of said restriction activity can be obtained and introduced into the host cells in active inhibitory form are suitable for use in the methods of the invention. The invention comprises both methods for using any host cells having a prokaryotic R-M system, whether this R-M system is naturally occurring or has been introduced using molecular genetic techniques known in the art, and methods for using eukaryotic R-M-type systems which result in restriction of transforming DNA in the host cell.

As discussed by Noreen E. Murray [*Microbiol. Molec. Biol. Rev.*, 64: 412–434, 2000; *Microbiology*, 148: 3–20, 2002] and Robert Yuan [*Ann. Rev. Biochem.*, 50: 285–315, 1981], and in the 3 $^{rd}$ edition of Sambrook and Russell's *Molecular Cloning—A Laboratory Manual*, all of which are incorporated herein by reference, three types of R-M systems (designated Types I, II and III) are currently known for prokaryotic cells. The present invention comprises methods to improve transformation efficiency by unmodified transforming DNA of Eubacteria and Archaebacteria host cells having at least one R-M system selected from among any of these three types of R-M systems, wherein the transforming DNA has at least one site which, in the absence of an inhibitor for the restriction activity of the host cell, would be restricted in the host cell. Murray [Ibid] and Yuan [ibid] disclose the characteristics and methods (and references therefor) for detecting the presence of and assaying for different types of R-M systems and restriction activities, which methods are incorporated herein by reference. Many of these methods are somewhat laborious and can be complicated, and knowledge of the characteristics and identity of the R-M system(s) in a particular host cell strain may not be a primary interest of an investigator who wishes to transform the host cells for a particular purpose.

The methods of the present invention can be used without the investigator knowing the identity of the R-M system(s) in the host cells used. In fact, there are several reasons why it would be preferable to apply the methods of the present invention without identifying or characterizing or assaying for the R-M system or restriction activity of the host cell used, including: (1) the R-M systems of many strains of prokaryotic host cells are unknown; (2) the R-M systems can vary even for different isolates of the same species of host cell; (3) some R-M systems are encoded by one or more plasmids, which may be transmissible between different strains; and (4) some host cells, such as the previously discussed example of *H. pylori*, can have more than one R-M system in the same cell.

Fortunately, some inhibitors of restriction activity can be used in methods of the invention for inhibiting the restriction activity of different R-M enzymes in different organisms. For example, some inhibitors can be used to inhibit restriction activity of most or all Type I systems. Thus, in many cases, it is easier to simply use the methods of the invention than to try to identify or characterize the R-M system(s) of the host cells. Further, since, for example, about half of the bacterial genomes examined had genes which encoded polypeptides homologous to Type I R-M systems [Murray, N. E., op cit], indicating that such Type I R-M systems are widespread in nature, there is a high likelihood that use of a method of the invention will be successful in increasing transformation efficiency by unmodified transforming DNA even without knowing the identity or characteristics of the R-M system of the host cells. If the inhibitor used is not effective in inhibiting the restriction activity of the particular host cells used, little additional time will be lost in testing another potential inhibitor of the invention, and overall, little time will be lost even if none of the inhibitors tested is effective. In that case, the investigator can simply try other suitable inhibitors of the invention, such as, but not limited to, the inhibitors described below, in order to inhibit the restriction activity of a particular host cell.

Inhibitors of the Restriction Activity of R-M Systems of the Invention

The present invention comprises any inhibitor of the restriction activity of an R-M system, which inhibitor can be introduced into a host cell so as to improve transformation efficiency of the host cell by unmodified transforming DNA by reducing or blocking restriction of the unmodified transforming DNA during transformation. By way of example, but not of limitation, an inhibitor of the invention can be a negatively charged polypeptide that binds to the host cell R-M system so as to improve transformation efficiency of the host cell by unmodified transforming DNA by reducing or blocking restriction of the unmodified transforming DNA during transformation. A "polypeptide" as used herein refers to a polymer of amino acids; thus, peptides, oligopeptides, and proteins are included within the definition of polypeptide.

In another embodiment of the invention, the inhibitor can be a polypeptide encoded by a bacteriophage gene that binds to the host cell R-M system so as to improve transformation efficiency of the host cell by unmodified transforming DNA by reducing or blocking restriction of the unmodified transforming DNA during transformation. In a preferred embodiment of the invention, the inhibitor is a polypeptide encoded by a T7-like bacteriophage gene. The genetic organization of all T7-like phages that have been examined has been found to be essentially the same as that of T7. Examples of T7-like phages according to the invention include, but are not limited to *Escherichia coli* phages T3, phi.I, phi.II, W31, H, Y, A1, 122, cro, C21, C22, and C23; *Pseudomonas putida* phage gh-1; *Salmonella typhimurium* phage SP6; *Serratia marcescens* phages IV; *Citrobacter* phage ViIII; and *Klebsiella* phage No. 11 [Hausmann, *Current Topics in Microbiology and Immunology*, 75: 77–109, 1976; Korsten, et al., *J. Gen. Virol.*, 43: 57–73, 1975; Dunn, et al., *Nature New Biology*, 230: 94–96,1971; Towle, et al., *J. Biol. Chem.*, 250:1723–1733, 1975; Butler and Chamberlin, *J. Biol. Chem.*, 257: 5772–5778, 1982]. In a most preferred embodiment of the invention, the inhibitor is an OCR protein encoded by the 0.3 ocr gene of bacteriophage T7 or bacteriophage T3. However, the invention is not limited to inhibitor of restriction encoded by T7-like phages and inhibitors encoded by other phages are also intended to be within the scope of the invention. As defined herein, an OCR protein comprises any naturally-occurring polypeptide which is encoded by a bacteriophage genome, wherein said polypeptide overcomes classical restriction of unmodified transforming DNA in a bacterial cell that can be infected by said bacteriophage by binding to an R-M system of said bacterial cell so as to inhibit the restriction activity of said R-M system. Whenever the inventors refer to T7 or T3 OCR Protein, or to the genes therefor, in the specification of the invention herein, it will be understood that the invention also includes other OCR proteins, and their respective genes, wherein said OCR proteins inhibit the restriction activity of an R-M system in a host cell.

In another embodiment of the invention, the inhibitor of the invention can be a negatively charged polypeptide encoded by a naturally-occurring transmissible or conjugative plasmid, which polypeptide binds to the host cell R-M system so as to improve transformation efficiency of the host cell by unmodified transforming DNA by reducing or blocking restriction of the unmodified transforming DNA during transformation. Preferably, the polypeptide is a negatively charged protein which mimics DNA and binds to the R-M enzyme system so as to inhibit restriction activity of said enzyme system in the host cell. In a preferred embodiment, the inhibitor is a polypeptide encoded by a gene selected from among an ardA gene, an ardB gene, and an ardC gene [Belogurov, A. A. et al., *J. Mol. Biol*, 296: 969–977, 2000]. Belogurov et al. reported that several ArdA, ArdB, and ArdC anti-restrictive proteins have a common "anti-restriction" domain, which appeared to correlate with anti-restriction activity of the proteins [ibid; Belogurov, A. A., and Delver, E. P., *Nucleic Acids Res.*, 23: 785–787, 1995]. As defined herein, an Ard protein comprises any polypeptide which is encoded by a naturally-occurring transmissible or conjugative plasmid or replicon, wherein said polypeptide, when present in a Eubacterial or Archaebacterial host cell, alleviates, reduces or blocks restriction of unmodified DNA which, except for the presence of said polypeptide, would be restricted by the restriction activity of an R-M system of said host cell. Whenever the inventors refer to ArdA, ArdB, or ArdC proteins, or to the genes therefor, in the specification of the invention herein, it will be understood that the invention also includes other Ard proteins, and their respective genes, wherein said Ard proteins inhibit the restriction activity of an R-M system in a host cell. An inhibitor of the invention can comprise any acidic or negatively-charged polypeptide, wherein said polypeptide comprises at least one amino acid domain having an amino acid sequence and three-dimensional structure, wherein said domain binds to the R-M system so as to inhibit its restriction activity with respect to unmodified transforming DNA. Preferably, the inhibitor is added to competent host cells prior to or concurrent with addition of the transforming DNA. Most preferably, the inhibitor is added to electrocompetent host cells and both the inhibitor and the transforming DNA are incorporated into the host cells by electroporation.

It has been reported that both the T7 0.3 ocr gene product and ArdA protein inhibit multiple Type I R-M enzymes [In:

Murray, N. E., *Microbiology,* 148: 3–20, 2002]. However, some embodiments of the invention, especially when the R-M system of the host cell is unknown and/or in cases where there are known to be or may be more than one R-M system in a particular host cell, more than one inhibitor of restriction activity of the R-M systems of the host cell are used simultaneously to improve transformation efficiency by unmodified transforming DNA of the invention.

Another embodiment of the invention is an inhibitor of restriction comprising a protein which is responsible for restriction alleviation in a cell, as discussed by Noreen Murray [*Microbiol. Molec. Biol. Rev.,* 64: 412–434, 2000 (especially pp. 423–425)], incorporated herein by reference. Thus, one embodiment of the invention is an inhibitor comprising a protein responsible for alleviation of restriction activity wherein the protein is ClpXP protease encoded by clpX and clpP genes.

Although the inhibitors described herein above are preferred inhibitors of restriction activity of an R-M system of the invention, the invention is not limited to these inhibitor polypeptides. The inhibitor can be a polypeptide encoded by any gene in a naturally-occurring bacteriophage or in an autonomously-replicating DNA molecule, such as a transmissible or conjugative plasmid, in a *Eubacterium* or an *Archaebacterium*, wherein said inhibitor improves transformation efficiency of the host cell by unmodified transforming DNA by reducing or blocking restriction of the unmodified transforming DNA during transformation.

Inhibitors of the present invention are not limited to polypeptide molecules, although negatively charged polypeptide molecules are preferred inhibitors of the invention. Thus, an inhibitor of the invention can also be a nucleic acid, polynucleotide, oligonucleotide or a segment of a nucleic acid or polynucleotide, including nucleic acids composed of either DNA or RNA, or both DNA and RNA mononucleosides, including non-naturally occurring DNA or RNA mononucleosides. [The inventors use the term "non-naturally occurring" herein to refer to nucleic acid bases, sugars and internucleoside linkages which are not those which are common in most cells in nature, even though some of them could occur naturally in some cells or under some conditions; this term is used to minimize the use of the term "modified" with respect to such bases, sugars or internucleoside linkages in order to avoid confusion with "unmodified" transforming DNA of the invention. As discussed earlier, the modification enzymes of an R-M system that protect the DNA from digestion are generally DNA methyltransferases which catalyze methylation of specific nucleic acid bases within the target sequence that is digested by the endonuclease, resulting in DNA that is "modified" with respect to that R-M system. The term "unmodified transforming DNA" as used herein refers to DNA that lacks methyl groups or other modifications, which usually, but not always, have been added by the modification activity of an R-M system.]

The invention does not limit the composition of the nucleic acids or polynucleotides comprising inhibitors of the restriction activity of an R-M system so long as each said nucleic acid functions for its intended use. Preferably the oligonucleotide or polynucleotide improves transformation efficiency of the host cell by unmodified transforming DNA by reducing or blocking restriction of the unmodified transforming DNA during transformation. For a variety of reasons, a nucleic acid or polynucleotide of the invention may comprise naturally-occurring nucleic acid bases, sugar moieties, or internucleoside linkages or one or more non-naturally occurring nucleic acid bases, sugar moieties, or internucleoside linkages. By way of example, one reason for using nucleic acids or polynucleotides that contain non-naturally occurring bases, sugar moieties, or internucleoside linkages is to change the susceptibility of the polynucleotide to one or more nucleases. By way of example, the non-naturally occurring portions of the polynucleotide or oligonucleotide can include, but are not limited to, one or more phosphorothioate, phosphorodithioate, phosphoramidothioate, phosphoramidate, phosphordiamidate, methylphosphonate, alkyl phosphotriester, phosphoroselenate, phosphorodiselenate or formacetal, or analogs thereof, inter-sugar (backbone) linkages, some of which are resistant to some nucleases.

With respect to nucleic acids or polynucleotides of the invention, one or more of the sugar moieties can comprise ribose or 2'-deoxyribose, or alternatively, one or more of the sugar moieties can be some other sugar moiety, such as, but not limited to, 2'-fluoro-2'-deoxyribose or 2'-O-methyl-ribose, which provide resistance to some nucleases.

The invention also does not limit the composition of the nucleic acid bases in polynucleotides or oligonucleotides comprising inhibitors of the restriction activity of an R-M system so long as each said nucleic acid functions for its intended use. By way of example, but not of limitation, the nucleic acid bases in the mononucleotides may comprise guanine, adenine, uracil, thymine, or cytidine, or alternatively, one or more of the nucleic acid bases may comprise xanthine, allyamino-uracil, hypoxanthine, 2-aminoadenine, 6-methyl and other alkyl adenines, 2-propyl and other alkyl adenines, 5-halouracil, 5-halo cytosine, 5-propynyl uracil, 5-propynyl cytosine, 7-deazaadenine, 7-deazaguanine, 7-deaza-7-methyl-adenine, 7-deaza-7-methyl-guanine, 7-deaza-7-propynyl-adenine, 7-deaza-7-propynyl-guanine and other 7-deaza-7-alkyl or 7-aryl purines, N2-alkyl-guanine, N2-alkyl-2-amino-adenine, purine 6-aza uracil, 6-aza cytosine and 6-aza thymine, 5-uracil (pseudo uracil), 4-thiouracil, 8-halo adenine, 8-amino-adenine, 8-thiol adenine, 8-thiolalkyl adenines, 8-hydroxyl adenine and other 8-substituted adenines and 8-halo guanines, 8-amino-guanine, 8-thiol guanine, 8-thiolalkyl guanines, 8-hydroxyl guanine and other 8 substituted guanines, other aza and deaza uracils, other aza and deaza thymidines, other aza and deaza cytosine, aza and deaza adenines, aza and deaza guanines or 5-trifluoromethyl uracil and 5-trifluorocytosine. Still further, they may comprise a nucleic acid base that is derivatized with a biotin moiety, a digoxigenin moiety, a fluorescent or chemiluminescent moiety, a quenching moiety or some other moiety. The invention is not limited to the nucleic acid bases listed; this list is given to show the broad range of bases which may be used for a particular purpose in an assay.

A variety of methods are known in the art for making nucleic acids having a particular sequence or that contain particular nucleic acid bases, sugars, internucleoside linkages, chemical moieties, and other compositions and characteristics. Any one or any combination of these methods can be used to make a nucleic acid, polynucleotide, or oligonucleotide for the present invention. Said methods include, but are not limited to: (1) chemical synthesis (usually, but not always, using a nucleic acid synthesizer instrument); (2) post-synthesis chemical modification or derivatization; (3) cloning of a naturally occurring or synthetic nucleic acid in a nucleic acid cloning vector (e.g., see Sambrook, et al., Molecular Cloning: A Laboratory Approach $2^{nd}$ ed., Cold Spring Harbor Laboratory Press, 1989) such as, but not limited to a plasmid, bacteriophage (e.g., m13 or lamda), phagemid, cosmid, fosmid, YAC, or BAC cloning vector, including vectors for producing single-stranded DNA; (4) primer extension using an enzyme with DNA template-dependent DNA polymerase activity, such as, but not limited to, Klenow, T4, T7, rBst, Taq, Tfl, or Tth DNA polymerases, including mutated, truncated (e.g., exo-minus), or chemically-modified forms of such enzymes; (5) PCR (e.g., see Dieffenbach, C. W., and Dveksler, eds., PCR Primer: A Laboratory Manual, 1995, Cold Spring Harbor Laboratory Press, Cold Spring Harbor, N.Y.); (6) reverse transcription (including both isothermal synthesis and RT-PCR) using an enzyme with reverse transcriptase activity, such as, but not limited to, reverse transcriptases derived from avian myeloblasosis virus (AMV), Maloney murine leukemia virus (MMLV), *Bacillus stearothermophilus* (rBst), *Thermus thermophilus* (Tth); (7) in vitro transcription using an enzyme with RNA polymerase activity, such as, but not limited to, SP6, T3, or T7 RNA polymerase, Tth RNA polymerase, *E. coli* RNA polymerase, or another enzyme; (8) use of restriction enzymes and/or modifying enzymes, including, but not limited to exo- or endonucleases, kinases, ligases, phosphatases, methylases, glycosylases, terminal transferases, including kits containing such modifying enzymes and other reagents for making particular modifications in nucleic acids; (9) use of polynucleotide phosphorylases to make new randomized nucleic acids; (10) other compositions, such as, but not limited to, a ribozyme ligase to join RNA molecules; and/or (11) any combination of any of the above or other techniques known in the art. Oligonucleotides and polynucleotides, including chimeric (i.e., composite) molecules and oligonucleotides with non-naturally-occurring bases, sugars, and internucleoside linkages are commercially available (e.g., see the 2000 Product and Service Catalog, TriLink Biotechnologies, San Diego, Calif., USA; www.trilinkbiotech.com).

There are a variety of methods for finding an oligonucleotide or polynucleotide which has activity as an inhibitor of the restriction activity of an R-M system according to the invention. For example, since the region of OCR Protein that binds to the restriction domain of a Type I R-M system has been shown to resemble the bent structure of DNA bound to the Type I R-M complex [Atanasiu, O. B., et al., *Nucl. Acids Res.*, 29: 3059–3068, 2001; Walkinshaw, M. D., et al., "Structure of ocr from bacteriophage T7, a protein that mimics B-form DNA," Molec. *Cell*, 9: 187–194, 2002] and also, because the nucleotide recognition sequences for the restriction activity of some R-M systems is known, an inhibitor of restriction activity of the R-M system can be made by rational design in some cases. By way of example, an oligonucleotide can be made which has similar structure and nucleic acid base sequence to that which is recognized by the active site of the restriction enzyme domain of the R-M system, but wherein the oligonucleotide comprises modified sugar moieties and/or internucleoside linkages, as discussed herein, which cannot be digested by the restriction enzyme.

Alternatively, a method termed "SELEX," as described by Gold and Tuerk in U.S. Pat. No. 5,270,163, can be used to select a nucleic acid for use as an inhibitor according to the invention. SELEX permits selection of a nucleic acid molecule that has high affinity for a specific analyte from a large population nucleic acid molecules, at least a portion of which have a randomized sequence. For example, a population of all possible randomized 25-mer oligonucleotides (i.e., having each of four possible nucleic acid bases at every position) will contain $4^{25}$ (or $10^{15}$) different nucleic acid molecules, each of which has a different three-dimensional structure and different analyte binding properties. SELEX can be used, according to the methods described in U.S. Pat. Nos. 5,270,163; 5,567,588; 5,580,737; 5,587,468; 5,683,867; 5,696,249; 5,723,594; 5,773,598; 5,817,785; 5,861,254; 5,958,691; 5,998,142; 6,001,577; 6,013,443; 6,030,776; and 6,300,074, incorporated herein by reference, in order to select an analyte-binding nucleic acid with high affinity for the restriction activity domain of the R-M system of the host cell. A polynucleotide or oligonucleotide inhibitor of the invention that is obtained using SELEX may comprise naturally occurring nucleic acid bases, sugar moieties, or internucleoside linkages or one or more non-naturally occurring nucleic acid bases, sugar moieties, or internucleoside linkages.

By way of example, but not of limitation, SELEX can be used to find an inhibitor of restriction activity as follows: If the R-M system and a suitable nucleic acid substrate for which the R-M system has restriction activity can be obtained in purified form, then the substrate can be incubated with an active form of the R-M system under suitable restriction activity reaction conditions and the restriction activity of the R-M system on the substrate can be assayed in vitro by gel electrophoresis. Then, for example, all possible randomized 25-mer oligonucleotides can be screened using the SELEX procedure to find suitable candidate oligonucleotide inhibitors that inhibit the restriction activity of the R-M system. Among those candidates, the best in vitro inhibitors can be screened by in vivo transformation in order to find inhibitors that increase transformation efficiency of a host cell by unmodified transforming DNA having a selectable marker, such as an antibiotic resistance marker. By way of example, but not of limitation, an inhibitor of restriction activity of an R-M system of the invention that comprises DNA and/or RNA can be obtained using SELEX in a manner similar to that described for obtaining an inhibitor for Taq and Tth DNA polymerases [U.S. Pat. No. 6,020,130]; these inhibitors of Taq and Tth DNA polymerase activity exemplify that SELEX can be used to obtain an inhibitor for an enzyme that interacts with a DNA molecule, which is also the case for an inhibitor of restriction activity of an R-M system of the present invention. Further, those with skill in the art will know that DNA, including DNA that is an inhibitor of the restriction activity of an R-M system that is selected using SELEX according to the invention, can be used to transform a chemically-competent host cell, or to transform an electrocompetent host cell by electroporation, or to transform other cells by other means, using methods similar to those known in the art.

Once selected using SELEX, nucleic acid inhibitor molecules can be made by any of numerous known in vivo or in vitro techniques, including, by way of example, but not of limitation, automated nucleic acid synthesis techniques, PCR, or in vitro transcription, including in vitro transcription using T7 R&DNA.sup.TM. Polymerase (EPICENTRE), which incorporates non-canonical nucleotides as well as canonical nucleotides [U.S. Pat. Nos. 5,849,546; and 6,107,037].

In still another embodiment of the invention, the inhibitor of restriction activity that improves transformation efficiency of a host cell by unmodified DNA is a "Peptide Nucleic Acid" (PNA) molecule which, following its introduction into the host cell, binds to the host cell's R-M system so as to reduce or block restriction of the unmodified transforming DNA during transformation. A PNA molecule or a molecule comprising both a nucleic acid and a PNA, as described in U.S. Pat. Nos. 5,539,082; 5,641,625; 5,700,922; 5,705,333; 5,714,331; 5,719,262; 5,736,336; 5,773, 571; 5,786,461; 5,817,811; 5,977,296; 5,986,053; 6,015,887; and 6,020,126 (and references therein), all of which are incorporated herein by reference, can also be used as an inhibitor of the invention. In general, a PNA molecule is a nucleic acid analog consisting of a backbone comprising, for example, N-(2-aminoethyl)glycine units, to each of which a nucleic acid base is linked through a suitable linker, such as, but not limited to an aza, amido, ureido, or methylene carbonyl linker. Since PNA is not naturally occurring, PNA molecules are highly resistant to protease and nuclease activity. PNA for use as an inhibitor of the restriction activity of an R-M system can be prepared according to methods know in the art, such as, but not limited to, methods described in the above-mentioned patents, and references therein.

The invention also contemplates that a combinatorial library of randomized peptide nucleic acids prepared by a method such as, but not limited to, the methods described in U.S. Pat. Nos. 5,539,083; 5,831,014; and 5,864,010, can be used to prepare inhibitors of restriction activity. As is the case for the SELEX method with nucleic acids, randomized peptide or peptide nucleic acid libraries are made to contain molecules with a very large number of different binding affinities for an analyte. After selection of an appropriate affinity molecule for an analyte from a library, the selected affinity molecule can be used in the invention as an inhibitor. A PNA inhibitor of restriction activity of an R-M system according to the invention will have a net negative charge and will bind tightly to the same domain of the enzyme responsible for restriction activity of an R-M system that recognizes and/or cleaves a nucleotide sequence in unmodified DNA. PNA molecules that are suitable for use as inhibitors in the invention can be identified and selected using similar screening techniques to those used to find and select an oligonucleotide inhibitor using SELEX, as discussed above.

Finally, in still another embodiment of the invention, the inhibitor that improves transformation efficiency of a host cell by unmodified DNA is a chemical molecule having negatively charged moieties and which molecule binds to the host cell's R-M system so as to reduce or block restriction of the unmodified transforming DNA during transformation. An inhibitor of restriction activity of an R-M system comprising a chemical molecule according to the invention will have a net negative charge and will bind tightly to the same domain of the enzyme responsible for restriction activity of an R-M system that recognizes and/or cleaves a nucleotide sequence in unmodified DNA.

In general, an inhibitor of restriction activity of the invention, whatever its type, can be identified as follows: If the R-M system and a suitable nucleic acid substrate for which the R-M system has restriction activity are known and can be obtained in purified forms, then the substrate can be incubated with an active form of the restriction enzyme of the R-M system under suitable restriction activity reaction conditions and the restriction activity of the R-M system on the substrate can be assayed in vitro by gel electrophoresis or another means. Then, each substance that is a potential inhibitor of restriction activity can be added to the restriction activity reaction in order to determine if it inhibits digestion of the unmodified DNA substrate. A range of concentrations of each substance can be assayed in this way. Among those candidates, the best in vitro inhibitors can be screened for their effects in vivo by assaying for their ability to increase transformation efficiency of a host cell by unmodified transforming DNA having a selectable marker, such as an antibiotic resistance marker; for this assay, suitable strains of electrocompetent host cells, each of which has a single known type of R-M system and a single restriction specificity should be used. Some suitable host cells and representative effects of an R-M inhibitor, such as the OCR Protein with respect to inhibition of Type I R-M systems, can be ascertained by reading the specifications and examples herein. Those with skill in the art will know or will know how to find and identify other strains with other restriction activities for use in assaying for potential inhibitors of restriction activity for use in the methods of the invention. With respect to the quantities of a substance that should be assayed for activity as an inhibitor of restriction activity, approximately one microgram up to about five micrograms is a suitable amount to assay for a potential polypeptide or protein inhibitor with respect to an electroporation in vivo transformation assay with an electrocompetent host cell, although the invention is not limited to those amounts of inhibitor. Amounts of a polypeptide substance greater than about five micrograms are likely to result in arcing during electroporation, which is harmful to the cells. However, it may be possible to assay higher amounts of a substance as a potential inhibitor when other methods of transformation are used. With respect to substances other than polypeptides that are assayed for their ability to increase transformation efficiency in vivo, an amount of the substance that is equivalent on a mole basis to about one microgram of OCR Protein up to about five times that amount is a suitable range.

In general, the method for introducing the inhibitor of restriction activity of the R-M system is the same as the method used for transformation of the host cells with unmodified transforming DNA. Thus, a preferred method for introducing an inhibitor of restriction activity into most host cells is by electroporation. In most embodiments of the invention, the inhibitor is introduced into the host cells at the same time as the unmodified transforming DNA is introduced. However, in some embodiments of the invention, the inhibitor can be introduced into the host cell prior to transformation with the unmodified transforming DNA.

Methods of Transformation of the Invention

Conditions, mechanisms and methods for achieving both natural and artificial transformation of host cells from different organisms has been reviewed [Smith, H. O., et al., "Genetic Transformation," In: *Ann. Rev. Biochem.,* 50: 41–68, 1981), which are incorporated herein by reference. Additional information on methods related to cloning and transformation are described or cited by Joseph Sambrook and David W. Russell [*Molecular Cloning—A Laboratory Manual Volumes* 1–3, Third Edition, Cold Spring Harbor Laboratory Press, Cold Spring Harbor, N.Y., 2001], also incorporated herein by reference. Still other methods for improving transformation of different particular types of cells are commonly known in the art and are readily obtained from the scientific literature. Many types of cells are treated with compounds, such as, but not limited to, calcium or rubidium salts, and/or grown under other conditions which increase their ability to take up DNA for transformation, in which case the cells are referred to as "competent cells." Some strains of competent cells, including both chemically competent and electrocompetent cells (meaning cells which have increased ability to take up DNA during electroporation, discussed below), are commercially available from various sources. However, for most types of cells, when competent cells are needed, they must be prepared using methods based on information in the scientific literature and/or obtained empirically by experimentation. The invention is not limited to any particular method for transformation so long as the method used permits introduction and incorporation of the transforming DNA into the host cells in a heritable form. If the inhibitor of restriction activity of the host cell's R-M system is introduced into the cell at the same time as the transforming DNA, the transformation method used must not result in inactivation of the inhibitor with respect to its ability to inhibit the restriction activity of the R-M system.

In an especially preferred embodiment of the invention, the method of transformation is by electroporation of the host cells. In this method, an electrical pulse destabilizes the cell membrane and results in formation of transient pores through which the transforming DNA can pass. Some conditions and methods of electroporation are discussed by Sambrook and Russell [ibid, see especially pp. 1.25–1.26, 1.119–1.122, 1.162, 4.3, 4.4. 4.46–4.52, 11.85–11.86, 16.33–16.36, and 16.54–16.57), incorporated herein by reference. Additional conditions and methods are known in the art and can be found in the scientific literature.

Transforming DNA of the Invention

In some embodiments of the invention, the transforming DNA, meaning the DNA used for transformation of the host cell, comprises a vector DNA. In most cases the transforming DNA will comprise a gene or other DNA which is desirable to replicate and/or to express in the host cells in addition to the vector DNA, and thus, comprises a recombinant vector DNA. As used herein, a "vector" is a DNA molecule in which other DNA, including, but not limited to "foreign" or "heterologous" DNA, can be operably joined so as to form a DNA molecule which can replicate autonomously following its introduction into a host cell. The words "foreign" or "heterologous" refer to the fact that the DNA which is operably joined to the vector is not normally present in the host cell in which it is replicated. The most common method by which the DNA is "operably joined" to a vector is by covalent joining of compatible ends by means of an enzyme referred to as a ligase, such as, but not limited to, T4 DNA ligase, by a process referred to as "ligation." Alternatively, as is well known in the art, the DNA molecules can be joined by means of an intermediate formed using an enzyme with topoisomerase I activity. Transforming DNA molecules comprising vectors can also be obtained by other methods, such as, but not limited to, chemical synthesis using a DNA or oligonucleotide synthesizer. The process of joining a DNA molecule into a vector and then replicating this molecule in a host cell is referred to as "molecular cloning," and a product of this process is referred to as a "clone." The methods of the present invention are not limited to a particular vector or host cell, but are intended to apply to any vector which is used to transform a host cell in which the vector can replicate, unless said vector is a suicide vector, in which case, the vector need not be capable of replication in the host cell. By way of example, but not of limitation, a vector of the invention can be a single-copy or multi-copy vector, such as but not limited to, a BAC (bacterial artificial chromosome), a fosmid, a cosmid, a plasmid, a suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate. As used herein, the word "replicate" refers to the fact that the vector and the DNA to which it is operably joined is copied or reproduced or duplicated in the host cell by a process called "replication." The site on the vector DNA at which replication begins is referred to as the "origin of replication." An origin of replication which requires the presence of another protein or another molecule in order for replication to occur is referred to as a "conditional origin of replication." A conditional origin of replication permits one to control replication by providing a means for controlling the expression or properties of the protein or other molecule which is required for replication from the ori. The number copies of a particular vector or of a clone in a particular vector varies based on a different factors, including, but not limit to, the sequence and structure of a particular origin of replication and the structure, amount, and properties of proteins which interact with the origin.

In some preferred embodiments of the invention, the transforming DNA is isolated from one type of cell for use in transforming another type of cell, in which case the transforming DNA from the first type of cell is unmodified with respect to the second type of cell. The DNA from the first type of cell can be naturally-occurring DNA from the cell or it can be a DNA that has been cloned or otherwise introduced into that cell. By way of example, but not of limitation, the unmodified DNA from the first type of cell can be present in a shuttle vector. A "shuttle vector" is a vector, such as a plasmid, which has either an origin of replication that functions in two different types of host cells, or two separate origins of replication, one for each of two unlike hosts. Some embodiments of the invention comprise methods, compositions, and kits for improving transformation of host cells with unmodified DNA in a shuttle vector, as well as unmodified DNA in another type of vector or that is naturally occurring.

In addition, although most embodiments of the invention comprise methods or compositions or kits for improving heritable transformation by an unmodified transforming DNA, some embodiments of the invention also comprise methods, compositions and kits in which the unmodified DNA which is introduced into the host cell is not incorporated in a heritable form. By way of example, but not of limitation, the unmodified DNA can be introduced into the host cell so as to obtain transient expression of a gene on a suicide vector, such as a suicide plasmid. A "suicide vector" refers to a vector, such as a plasmid, whose origin of replication is not functional in a particular bacterium or host into which it is introduced. Suicide plasmids may be used to express genes and their protein products for a limited period within the host. Thus, the invention also comprises methods, compositions and kits to improve introduction of DNA into host cells in a transient rather than a heritable form, as well as methods, compositions and kits to improve transient expression of genes in unmodified DNA that is introduced into host cells in a transient form. Under certain conditions, such as when the suicide vector comprises DNA, at least a portion of which is homologous to DNA in the host cell, the suicide vector can also be used to incorporate DNA into the host cell in a heritable form. For example, when a selectable marker is included within the suicide vector, the marker may be used to select for insertions of the plasmid into the chromosome or into other replicons present in the host. Methods, compositions and kits to improve heritable transformation of unmodified DNA in a suicide vector are also within the scope of the invention.

In other preferred embodiments of the invention, the transforming DNA used for transformation of the host cell comprises a transposon or an artificial transposon. "Transposition" is the process in which a transposable element is excised from one site and inserted into a second site on the same or another DNA molecule. Traditionally, a "transposon" was defined as a transposable element, meaning a DNA sequence that can move (transpose) from one site in DNA to another, that carries a gene encoding a transposase, as well as a gene or genes with other functions, such as resistance to antibiotics. However, recently Goryshin and Reznikoff [Goryshin, I Y, and Reznikoff, W S, "Tn5 in vitro transposition." *J. Biol. Chem.*, 273: 7367, 1998] showed that purified wild type and mutant forms of Tn5 transposase can catalyze in vitro transposition of any DNA that is between two properly oriented copies of a Tn5 transposase recognition sequence, which, with respect to Tn5 transposase, is usually called an "Outer End" or an "OE" sequence or an "Inner End" or an "IE" sequence, or a "Mosaic End" or an "ME" sequence, depending on the particular transposase used, but the recognition sequence for any particular transposase which can be used for the invention can also be referred to by a different name. In view of the findings of Goryshin and Reznikoff [ibid], it will be understood that the gene for the transposase does not need to be encoded by the transposon in order to obtain transposition, provided that a transposase is present in a reaction mixture in which the transposase has activity. Therefore, an "artificial transposon" according to the present invention and as used herein is any DNA that has properly-oriented recognition sequences for the transposase such that the DNA is capable of utilizing these recognition sequences so as to catalyze transposition. It is preferable that an artificial transposon of the invention does not encode a gene for a transposase because, in the absence of an active transposase gene, the transposon is not be able to transpose to a new location in the absence of added transposase enzyme and suitable reaction conditions. A "transposase" is an enzyme that catalyzes transposition. As used herein, the enzyme can be the wild type enzyme or a mutant form of the enzyme, which may, for example, give the enzyme a desirable property, such as, but not limited to, a higher activity or greater selectivity for its recognition sequence. One transposase used in the present invention is a hyperactive mutant form of Tn5 transposase, which is also sometimes referred to as "EZ::TN.sup.TM. Transposase," in which case the corresponding artificial transposon is referred to as an "EZ::TN.sup.TM. Transposon" (EPICENTRE). However, the invention is not limited to this enzyme or to transforming DNA comprising these transposons, and, unless otherwise specifically limited, other transposases are also intended to be within the scope of and covered by the invention. By way of example, but not of limitation, the invention also includes methods which use transposons and artificial transposons which can be transposed by Tn7 transposase [Biery, M. C., et al., "A simple in vitro Tn7-based transposition system with low target site selectivity for genome and gene analysis," *Nucleic Acid Res.*, 28: 1067–1077, 2000], Mu transposase [Surette, M. G., et al., "Transposomes: stable protein-DNA complexes involved in the in vitro transposition of bacteriophage Mu DNA," *Cell*, 49: 253–262, 1987; Haapa, S. S., et al., "An efficient and accurate integration of mini-Mu transposons in vitro: a general methodology for functional genetic analysis and molecular biology applications," *Nucleic Acids Res.*, 27: 2777–2784, 1999], Mariner transposase [Akerley, B. J., et al., "Systematic identification of essential genes by in vitro mariner mutagenesis," *Proc. Natl. Acad. Sci. USA*, 95: 8927–8932, 1998], Tn552 transposase [Griffin I V, T J, et al., "In vitro transposition of Tn552: a tool for DNA sequencing and mutagenesis," *Nucleic Acids Res.*, 27: 3859–3865, 1999], Tn10 transposase [Chalmers, R. M. and Kleckner, N., "Tn10/IS10 transposase, purification, activation, and in vitro reaction," *J. Biol. Chem.*, 269: 8029–8035, 1994], enzymes involved with retroviral DNA integration [Wei, S. M., et al., "A large nucleoprotein assembly at the ends of the viral DNA mediates retroviral DNA integration." *EMBO J.* 16: 7511–7520, 1997], enzymes involved with *Agrobacterium* T-DNA integration, and the like.

In other highly preferred embodiments of the invention, the transforming DNA used for transformation of the host cell comprises a synaptic complex between an artificial transposon and a transposase which recognizes the ends of the transposon [Goryshin and Reznikoff, U.S. Pat. No. 6,294,385]. A synaptic complex between an artificial Tn5 transposon and hyperactive Tn5 transposase has also been called a "Transposome.sup.TM. Complex" (EPICENTRE). A synaptic complex or Transposome complex is stable and does not carry out transposition in the absence of magnesium cations. However, upon transformation of the host cell by a method such as electroporation, the transposase is activated by intracellular magnesium cations and can catalyze in vivo transposition of the transposon into the DNA in the host cell [Goryshin, I Y, et al., "Insertional transposon mutagenesis by electroporation of released Tn5 transposition complexes," *Nature Biotechnol.*, 18: 97, 2000; Hoffman, L M, et al., "In vivo transposition of transposon/transposase complexes into the genome of *Saccharomyces*," *Current Genet.*, 35: 305, 1999; Hoffman, L M, et al., "Transposome insertional mutagenesis and direct sequencing of microbial genomes," *Genetica*, 108: 19–24, 2000]. A stable EZ::TN Transposome, which can even be stored for long periods in the freezer, is formed by incubating an EZ::TN Transposon and EZ::TN Transposase in the absence of Mg.sup.2+. Some EZ::TN Transposomes, such as EZ::TN <KAN-2> Tnp Transposome, are commercially available from EPICENTRE. Alternatively, custom EZ::TN Transposons can be prepared by using a Transposon Construction Vector such as pMOD.sup.TM. <MCS>, or by PCR using primers containing OE Sequences, or by ligating OE Sequences to the ends of the desired transposon DNA, as described for the EZ::TN.sup.TM. pMOD.sup.TM. <MCS> Transposon Construction Vector [Product Literature. No. 145, EPICENTRE Technologies, Madison, Wis.], incorporated herein by reference. Specific EZ::TN Transposons are designated herein as follows: The term "EZ::TN," which designates an artificial Tn5 transposon having hyperactive ME sequences, is followed by the names of each specific gene within the transposon, each of which is separated from the other by a forward slash (/); then, the names of all of the genes or genetic elements within the transposon are flanked by arrows (< >) which indicate the orientation of the terminal ME sequences; finally, this is followed by the word "Transposon" or "Transposome," as the case may be. For example, an "EZ::TN<oriV/KAN> Transposon" or an "EZ:: TN <oriV/KAN> Transposome" designates, respectively, an artificial Tn5 transposon or a Transposome.sup.TM. complex which has the oriV origin of replication and a kanamycin-resistance gene. As discussed above, transforming DNA of the invention comprising a synaptic complex is not limited to Tn5-type synaptic complexes. By way of example, but not of limitation, the transforming DNA can also comprise a synaptic complex prepared from a Mu transposase and an artificial transposon comprising DNA having Mu recognition sequences [Goryshin and Reznikoff, U.S. Pat. No. 6,294,385; Lamberg, A, et al., "Efficient insertion mutagenesis strategy for bacterial genomes involving electroporation of in vitro-assembled DNA transposition complexes of bacteriphage Mu," *Applied Environmental Microbiol.* 68: 705–712, 2002]. The transforming DNA can comprise a synaptic complex formed between any transposase and an artificial transposon which has recognition sequences recognized by said transposase, which synaptic complex is stable and does not catalyze transposition until the transposase is activated by some condition within the transformed host cell, such as, but not limited to, the presence of magnesium cations in the host cell. The synaptic complex, upon introduction into the host cell, catalyzes in vivo transposition of the transposon into DNA present in the host cell.

In other embodiments of the invention, the unmodified transforming DNA comprises a DNA polynucleotide, wherein the unmodified transforming DNA, upon introduction into the host cell, undergoes homologous recombination with DNA present in the host cell. In these embodiments, the regions of homology must be of sufficient size and have sequences so as to be recognized by the homologous recombination systems present in the host cell.

In other embodiments of the invention, the unmodified transforming DNA comprises a PCR amplification product. The PCR amplification product can comprise a transposon or an artificial transposon, or it can comprise a DNA polynucleotide, at least a portion of which has homology to DNA present in the host cell.

In certain embodiments of the invention, the unmodified transforming DNA comprises a gene or genes which are intended to result in a heritable change which is beneficial for a particular commercial or other application. By way of example, but not of limitation, lactic acid bacteria are well known to be important in the production of many different dairy products, such as yogurt, buttermilk, and other products, as well as in the fermentation of other products, such as pickled cucumbers and other products. Methods to improve transformation efficiency of lactic acid bacteria in order to improve the strains used for these purposes are highly desirable in the art. A commercial strain of *Lactococcus lactis* is known to have a single R-M system [Madsen, A., and Josephsen, J., "The LlaGI restriction and modification system of *Lactococcus lactis* consists of only one single polypeptide," *FEMS Microbiol. Letts.*, 200: 91–96, 2001]. The restriction activity of this type of cell can be inhibited by use of OCR Protein or other inhibitors of restriction activity using methods of the invention. Thus, the methods of the present invention can be used to improve strains and processes which use them. Without limiting the invention, some important embodiments of the invention comprise methods to improve transformation efficiency of a host cell comprising a lactic acid bacterium having an R-M system with unmodified transforming DNA. Those with knowledge in the art will know many other host cells which can be improved for use in commercial applications using the methods of the present invention, which are considered within the scope of the invention.

Preferred embodiments of the invention are transformed cells having new heritable genotypes and new properties, which cells are made by transforming host cells with a gene which encodes an inhibitor of the restriction activity of an R-M system in the cell using the methods of the invention described above. The cells can be of any type which can be transformed by any unmodified transforming DNA by using an inhibitor of the restriction activity of the host cell's R-M system.

Kits and Compositions for Improving Transformation Efficiency by Unmodified DNA of Host Cells Having an R-M System Still other embodiments of the invention are kits for improving transformation efficiency of a host cell having an R-M system with unmodified transforming DNA, wherein the kit comprises a preparation of an inhibitor which binds to the host cell's R-M system so as to reduce or block restriction of unmodified transforming DNA during transformation. Some embodiments of kits comprise a negatively charged polypeptide which binds to the host cell's R-M system so as to reduce or block restriction of unmodified transforming DNA during transformation. In some embodiments, the kits comprise a polypeptide encoded by a bacteriophage which binds to the host cell's R-M system so as to reduce or block restriction of unmodified transforming DNA during transformation. In a preferred embodiment, the kits comprise a polypeptide encoded by a T7-like bacteriophage which binds to the host cell's R-M system so as to reduce or block restriction of unmodified transforming DNA during transformation. In especially preferred embodiments, the kits comprise a preparation of an OCR protein encoded by the 0.3 ocr gene of bacteriophage T7 or bacteriophage T3. In other highly preferred embodiments, the kits comprise a preparation of a protein selected from among an ArdA Protein, an ArdB Protein, or an ArdC Protein. In another embodiment, the kit comprises a preparation of C/pXP Protein.

Preferred embodiments of the invention comprise kits for improving transformation efficiency of a host cell having an R-M system with unmodified transforming DNA, wherein the kit comprises a preparation of an inhibitor which binds to the host cell's R-M system so as to reduce or block restriction of unmodified transforming DNA during transformation and which kit is used to improve transformation efficiency by unmodified transforming DNA that is introduced into the host cell by electroporation. A kit of the invention can comprise any acidic or negatively-charged polypeptide, wherein said polypeptide comprises at least one amino acid domain having an amino acid sequence and three-dimensional structure, wherein said domain binds to the R-M system so as to inhibit its restriction activity with respect to unmodified transforming DNA. Preferably, the kit comprises an inhibitor that is added to competent host cells prior to or concurrent with addition of the transforming DNA. Most preferably, the kit comprises an inhibitor that is added to electrocompetent host cells and both the inhibitor and the transforming DNA are incorporated into the host cells by electroporation.

Other highly preferred embodiments of the invention are kits for improving electroporation transformation efficiency of a host cell having an R-M system with unmodified transforming DNA, wherein the kit comprises a preparation of an OCR protein encoded by the 0.3 ocr gene of bacteriophage T7 or bacteriophage T3.

Still other highly preferred embodiments of the invention are kits for improving electroporation transformation efficiency of a host cell having an R-M system with unmodified transforming DNA, wherein the kit comprises a preparation of an ArdA Protein, an ArdB Protein, or an ArdC Protein.

Other embodiments of the invention are kits for improving electroporation transformation efficiency of a host cell having an R-M system with unmodified transforming DNA, wherein the kit comprises a preparation of a ClpXP Protein.

Still other embodiments of the invention, comprise kits for improving transformation efficiency of a host cell having an R-M system with unmodified transforming DNA, wherein the kit comprises a preparation of a polynucleotide molecule prepared using SELEX, which polynucleotide molecule binds to the host cell's R-M system so as to reduce or block restriction of unmodified transforming DNA during transformation. In some embodiments, the inhibitor polynucleotide prepared using SELEX comprises DNA, in still other embodiments, the inhibitor polynucleotide prepared using SELEX comprises a polynucleotide selected from among an RNA molecule, a mixed RNA/DNA molecule, or a polynucleotide molecule comprising non-naturally-occurring sugars, bases and/or internucleoside linkages.

Other embodiments of the invention are kits for improving electroporation transformation efficiency of a host cell having an R-M system with unmodified transforming DNA, wherein the kit comprises a preparation of an inhibitor of the restriction activity of an R-M system which is obtained using SELEX.

Still other embodiments of the invention comprise kits for improving transformation efficiency, including electroporation transformation efficiency, of a host cell having an R-M system with unmodified transforming DNA, wherein the kit comprises a preparation of a Protein Nucleic Acid (PNA), wherein the PNA molecule binds to the host cell's R-M system so as to reduce or block restriction of unmodified transforming DNA during transformation.

Still other embodiments of the invention comprise kits for improving transformation efficiency, including electroporation transformation efficiency, of a host cell having an R-M system with unmodified transforming DNA, wherein the kit comprises a preparation of a chemical molecule having negatively charged moieties and which molecule binds to the host cell's R-M system so as to reduce or block restriction of unmodified transforming DNA during transformation.

Some embodiments are kits to provide conditions in which unmodified foreign nucleic acids are protected from restriction damage in the host cells during genetic transformation.

Some embodiments are kits to provide a protein that inhibits the R-M system of the host cells in vivo during genetic transformation. Still other embodiments of the invention are kits to provide increased transformation efficiencies of DNA comprising plasmids, fosmids, cosmids, BACs, other replicons, and transposons in bacterial strains having a Type I R-M system.

Still other embodiments of the invention are kits to provide increased transformation efficiencies of DNA comprising plasmids, fosmids, cosmids, BACs, other replicons, and transposons in bacterial strains having a Type II R-M system.

Still other embodiments of the invention are kits to provide increased transformation efficiencies of DNA comprising plasmids, fosmids, cosmids, BACs, other replicons, and transposons in bacterial strains having a Type III R-M system.

Highly preferred embodiments of the invention are kits to provide optimized systems for introduction of active undamaged transposon synaptic complexes comprising unmodified artificial transposons into host cells in order to obtain higher transposition efficiencies in vivo.

Still other preferred embodiments are kits to provide conditions in which unmodified foreign nucleic acids are protected from restriction damage following introduction into host cells in order to obtain transient gene expression of genes on the unmodified foreign DNA.

Other embodiments of the invention are kits for obtaining improved transient expression of genes on unmodified foreign DNA which is introduced into host cells by electroporation, wherein the kit comprises a preparation of an inhibitor of the restriction activity of an R-M system present in the host cells.

Methods for Obtaining Genetically Altered Host Cells Which Have Improved Transformation Efficiencies by Unmodified Transforming DNA A different embodiment of the invention is a method for obtaining a genetically altered host cell having improved transformation efficiency for unmodified transforming DNA, said method comprising: (1) introducing into a parent cell a first inhibitor of the restriction activity of the R-M system of said parent cell; and (2) transforming said parent cell with a transforming DNA comprising a gene which encodes a second inhibitor of the restriction activity of said R-M system of said parent cell, which second inhibitor of restriction activity encoded by said gene can be expressed in active form so as to inhibit the restriction activity of said R-M system under suitable conditions, and wherein said first and second inhibitors may be the same or different from each other. In some aspects of this embodiment of the invention, the parent cell is selected from the group consisting of Eubacteria or Archaebacteria. The parent cell of this embodiment can have at least one restriction and modification (R-M) system selected from among a Type I R-M system, a Type II R-M system, or a Type III R-M system, but the invention is not limited to only these R-M systems.

In embodiments of this aspect of the invention, the parent cells are transformed by a recombinant DNA molecule comprising a gene, which gene encodes an inhibitor of restriction activity of an R-M system, and which gene is capable of being expressed in the resulting host cell under suitable conditions. In one embodiment, the gene which encodes an inhibitor of the restriction activity of an R-M system is in a plasmid or bacteriophage vector or another vector. In another preferred embodiment, the gene encoding the inhibitor of restriction activity is in an artificial transposon. In most preferred embodiments, the gene encoding the inhibitor of restriction activity is in an artificial transposon comprising a synaptic complex. In other embodiments, the gene encoding an inhibitor of restriction activity is in a DNA molecule, at least a part of which has homology with DNA in the parent cell, which parent cell is capable of catalyzing homologous recombination.

In preferred embodiments of the invention, the gene in the recombinant DNA molecule which encodes the second inhibitor can be, but is not limited to, a 0.3 ocr gene of bacteriophage T3 or T7, or an ardA gene, an ardB gene, or an ardC gene, in which case, the unmodified recombinant DNA molecule having this gene may itself be incorporated into the parent cell by transformation using a first inhibitor of restriction activity of the R-M system of the parent cell, such as, but not limited to, a T7 or T3 OCR Protein or an ArdA Protein, an ArdB Protein, or an ArdC Protein, according to the methods of the invention. However, the invention is not limited to these genes or these inhibitors and other genes encoding inhibitors of restriction activity and other inhibitors of restriction activity of the parent cell's R-M system can also be used in the methods of the invention.

In some embodiments of the invention the gene which encodes the protein that is the second inhibitor of restriction is expressed conditionally in the resulting host cell. By way of example, but not of limitation, the inhibitor gene can be under the control of an araB promoter, in which case, expression of the gene can be induced by addition of arabinose to the culture medium of the host cells. The use of a conditional promoter permits induction of expression of the inhibitor protein only when it is needed to increase transformation efficiency during transformation by unmodified transforming DNA, thus retaining an active R-M system in the cell at other times to protect the cell from phages and other unwanted unmodified transforming DNA. Other inventors have used an inducible promoter, including an araB promoter, in order to express a protein which is downstream of (i.e., 3' of) the promoter on a replicable vector (E.g.s, U.S. Pat. Nos. 5,028,530; 6,242,219; and 6,274,344). However, in most embodiments of the present invention, an inducible promoter is used to express an inhibitor protein from a gene inserted into a host chromosome and is not used to express a gene on a replicable vector. Since the transcription promoter and other control elements required for expression can vary depending on the particular type of host cells, the invention is not limited with respect to the promoter or the method of obtaining expression following transformation of the parent cells with the inhibitor gene. The expression of an inhibitor gene of the invention can be achieved using any transcription promoter and expression system which is suitable for the host cells.

If a parent cell is transformed by an unmodified recombinant DNA which is capable of expressing the gene for an inhibitor of restriction activity using an artificial transposon comprising a synaptic complex between the transposon and a corresponding transposase which is capable of catalyzing transposition of said transposon, then the parent cell strain can be transformed to express the protein inhibitor encoded by said gene in a heritable manner. Thus, this transformed parent cell can be used subsequently as a host cell for transformation by other unmodified DNA molecules such as, but not limited to, other DNA molecules comprising plasmids or other replicons, bacteriophage DNA, transposons, or other polynucleotides, at least a part of which have homology with DNA in the host cell so as to be capable of homologous recombination in said host cell. If a transposon is used for transformation of the host cell expressing the inhibitor, it is desirable that the transposon uses a different transposase for transposition than the transposase used to make the host cell which expresses the inhibitor of restriction since subsequent transformation by a synaptic complex comprising the same transposase could potentially cause rearrangements or loss of the transposon in the host cell expressing the inhibitor protein. If the host cell expressing the inhibitor protein is made using a recombinant plasmid having an expressible gene for the inhibitor of restriction activity, then it may be desirable, although it is not essential, that plasmids used for subsequent transformation of the host cell expressing the inhibitor protein are compatible with the inhibitor-expressing plasmid or other vector.

There are also other variations of this embodiment of the invention in terms of the first inhibitor of the restriction activity of the R-M system of the parent cell and in terms of which second inhibitor of the restriction activity of said R-M system of said parent cell is encoded by the gene used to transform the parent cell. Thus, in some embodiments, at least one of the inhibitors is a negatively charged polypeptide that binds to the R-M system so as to reduce or block said restriction activity for unmodified transforming DNA. In some embodiments, at least one of the inhibitors of the restriction activity of the R-M system is a polypeptide encoded by a bacteriophage that binds to the R-M system so as to reduce or block said restriction activity for unmodified transforming DNA. In some embodiments at least one of the inhibitors of the restriction activity of the R-M system is a polypeptide encoded by a T7-like bacteriophage that binds to the R-M system so as to reduce or block said restriction activity for unmodified transforming DNA. In a most preferred embodiment, at least one of the inhibitors of the restriction activity of the R-M system comprises an OCR protein encoded by the 0.3 gene of bacteriophage T7 or bacteriophage T3. In another most preferred embodiment, at least one of the inhibitors of the restriction activity of the R-M system comprises a polypeptide encoded by a gene selected from among an ardA gene, an ardB gene, or an ardC gene. Other preferred embodiments comprise methods in which at least one of the inhibitors of the restriction activity of the R-M system comprises a polypeptide encoded by a gene in a naturally-occurring autonomously-replicating DNA molecule in a *Eubacterium* or an *Archaebacterium*. Thus, the inhibitor can be one that is encoded by any transmissible plasmid or other episome which is capable of binding to the restriction domain of an R-M enzyme or enzyme system so as to reduce of block the restriction activity for transforming DNA that is unmodified with respect to said R-M system.

In the most preferred embodiments of these aspects of the invention, both the first inhibitor of the restriction activity of the R-M system of the parent cell and the transforming DNA comprising a gene which encodes a second inhibitor of the restriction activity of said R-M system are introduced into the parent cell by electroporation. However, the invention is not limited to use of electroporation for this embodiment and any suitable method for introducing the first inhibitor of the restriction activity of an R-M system of the parent cell or for transforming the parent cell with the gene which encodes the second inhibitor of restriction activity can be used. Further, the method for introducing the first inhibitor and for transforming the gene for the second inhibitor can be the same or different.

As discussed above, in a preferred embodiment of this aspect of the invention, the transforming DNA comprising a gene which encodes a second inhibitor of the restriction activity of the R-M system of the parent cell comprises a transposon or an artificial transposon. In a most preferred embodiment, the transforming DNA comprising a gene which encodes a second inhibitor of the restriction activity of the R-M system of said parent cell comprises a synaptic complex between an artificial transposon and a transposase, which synaptic complex, upon introduction into the parent cell, catalyzes in vivo transposition of said transposon into DNA present in said parent cell. However, the invention is not limited to transforming DNA comprising a transposon or artificial transposon. The invention also includes embodiments in which the transforming DNA comprising a gene which encodes a second inhibitor of the restriction activity of the R-M system of said parent cell comprises a polynucleotide selected from the group comprising plasmids, suicide plasmids, shuttle vectors, cosmids, fosmids, oligonucleotides, replicons, amplicons, BACs, YACs, episomes, or mixtures thereof. In still other embodiments, the transforming DNA comprising a gene which encodes a second inhibitor of the restriction activity of the R-M system of said parent cell comprises a polynucleotide comprising DNA, at least a portion of which has homology to DNA present in the host cell, and in a preferred embodiment, the transforming DNA, upon introduction into the parent cell, undergoes homologous recombination with DNA present in the parent cell.

Kits and Compositions For Making Genetically Altered Host Cells Which Have Improved Transformation Efficiencies by Unmodified Transforming DNA The invention also comprises kits and compositions for making genetically altered host cells which have improved efficiencies of transformation by unmodified transforming DNA. By way of example, but not of limitation, the invention comprises a kit for making genetically altered host cells which have improved efficiencies of transformation by unmodified transforming DNA wherein the kit comprises: (1) a first inhibitor of the restriction activity of the parent cell's R-M system selected from among an OCR protein encoded by the 0.3 ocr gene of bacteriophage T7 or bacteriophage T3 and an ArdA Protein, an ArdB Protein, or an ArdC; and (2) a gene which encodes the second inhibitor of the restriction activity of the parent cell's R-M system selected from among an ocr gene of bacteriophage T7 or bacteriophage T3 and an ardA gene, an ardB gene, or an ardC gene. In one preferred embodiment of this kit of the invention, the gene which encodes the second inhibitor of the restriction activity of the parent cell's R-M system is selected from among an ocr gene of bacteriophage T7 or bacteriophage T3 and an ardA gene, an ardB gene, or an ardC gene, which gene comprises a transposon or an artificial transposon, and in a most preferred embodiment, the gene which encodes the second inhibitor of the restriction activity of the parent cell's R-M system comprises an artificial transposon, wherein said transposon comprises a synaptic complex with a transposase, which synaptic complex, upon introduction into the parent cell, catalyzes in vivo transposition of said transposon into DNA present in the parent cell. In another preferred embodiment, the gene which encodes the second inhibitor of the restriction activity of the parent cell's R-M system is selected from among an ocr gene of bacteriophage T7 or bacteriophage T3 and an ardA gene, an ardB gene, or an ardC gene, which gene comprises a transforming DNA which, upon introduction into the parent cell, undergoes homologous recombination with DNA present in said parent cell. In preferred embodiments of a kit of this aspect of the invention, both the first inhibitor of the restriction activity of the R-M system of the parent cell and the transforming DNA comprising a gene which encodes a second inhibitor of the restriction activity of said R-M system are introduced into the parent cell by electroporation.

Still other preferred embodiments of the invention are host cells with improved efficiency of transformation by unmodified transforming DNA, which host cells are made by genetically altering parent cells using the methods and/or kits described above. By way of example, genetically altered host cells with improved efficiency of transformation by unmodified transforming DNA can be made using these methods for lactic acid-producing bacteria as parent cells, which cells can be used for genetically improving the characteristics of the resulting host cells for commercial processes such as for producing dairy products or for other applications. However, the invention is not limited to improving lactic acid-producing bacteria. The invention can be used to make host cells with improved efficiency of transformation by unmodified transforming DNA from any suitable parent cell having an R-M system for which a suitable inhibitor of the restriction activity is available. Also, the method can be used to introduce any genetic improvement into the resulting host cells for any application.

Numerous modifications and alternative embodiments of the invention will be apparent to those skilled in the art in view of the foregoing description. Accordingly, this description is to be construed as illustrative only and is for the purpose of teaching those skilled in the art the best mode of carrying out the invention. The details of the host cells, inhibitors of restriction activity of R-M systems, and other aspects of the invention can be varied substantially without departing from the spirit of the invention, and the exclusive use of all modifications, which come within the scope of the appended claims, is reserved.

The present invention will be more clearly understood with reference to the following examples.

EXAMPLES

Example 1

Bacterial Strains and Growth Conditions

E. coli TransforMax™ EC100™ (F⁻ mcrA Δ(mrr-hs-dRMS-mcrBC) phi80dlacZ Δ M15 Δ lacX74 recA1 endA1 araD139 Δ (ara, leu)7697 galU ga/k lambda⁻ rpsL nupG) and TransforMax EC100™ pir-116 (F⁻ mcrA Δ mrr-hs-dRMS-mcrBC) phi80dlacZ ΔM15 Δ lacX74 recA1 endA1 araD139 Δ (ara, leu)7697 galU galK lambda⁻ rpsL nupG pir-116 (DHFR) electrocompetent cells were obtained from EPICENTRE (Madison, Wis.). *Salmonella typhimurium* LT2 and LB5000 ($r_{LT}$-, $r_{SA}$-, $r_{SB}$-) were obtained from Dr. Barry Hall (University of Rochester). *Agrobacterium tumefaciens* BAA-100 was obtained from the ATCC (Rockville, Md.). *E. coli* MG1655 was from Dr. Igor Goryshin (University of Wisconsin-Madison). All bacteria were grown in LB broth at 37° C., except that *Agrobacterium* was grown at 30° C.

Without limiting the invention, an example of a procedure for preparation of electrocompetent cells for use in electroporation is as follows: Inoculate 1 liter of autoclaved L. Broth (LB; Luria-Bertani), [10 g tryptone, 5 g yeast extract, & 5 g NaCl in 1 L water] with a 20 ml of an overnight-saturated culture of *E. coli*. Grow to late log phase ($A_{600}$=0.5–0.8) while shaking at 37° C. This takes about 3.5 hours. From this point on, keep cells as close as possible to 0.degree.C. Chill cells on ice 15–30 minutes and centrifuge in a cold rotor 4000×g for 15 minutes (4500 rpm, in the RC-5B SS-3 rotor). Discard as much of the supernatant as possible, even if some cells are removed in the process. Resuspend the pellet in 1 L ice-cold $H_2O$. Centrifuge as above. Resuspend in 0.5 L ice-cold $H_2O$, and centrifuge as above. Resuspend in 20 ml of ice-cold, sterile 10% glycerol in $H_2O$ and transfer to a 50-ml disposable Falcon tube. Centrifuge 3000 rpm, 4.degree.C., 15 minutes. Resuspend in 3 ml of ice-cold sterile 10% glycerol. The cell concentration should be about =1–3×10.sup.10/ml. Aliquot in 50-microliter volumes per microcentifuge tube. Freeze on dry ice and store at minus 70.degree.C. Cells are good for about 6 months.

Example 2

Electroporation Transformation Conditions

Electroporations were performed in 0.2-mm gap cuvettes with an Eppendorf Multiporator at a setting of 2500 volts, generating a time constant of approximately 5 ms. Outgrowth was for 45 min with shaking at 200 rpm.

Without limiting the invention, an example of a protocol for electroporation of electrocompetent cells is as follows: Thaw bacterial cells at room temperature and then place them on ice. Place sterile cuvettes and the white cuvette chamber slide on ice. Temperature is important because the probability of arcing increases with temperature. Mix 1–2 microliters of DNA in TE [10 mM Tris-HCl, pH 7.8 and 1 mM EDTA] with the cells. Use 100 pg of supercoiled plasmid DNA as a positive control (this should give about 200 colonies), and 0.5–1.0 ng (of vector) for a ligated construct. This may be increased to about 5 ng if low yields are obtained. Incubate on ice for 30–60 seconds. Set the Eppendorf Multiporator apparatus for 25 microFarad. Set the Pulse Controller to 2500 volts. Set the Gene Pulser to 2.50 kV for 2-mm cuvettes (or 1.5–1.8 kV for 1-mm cuvettes). Do not use the 4-mm cuvettes for bacteria. E. coli require a high field strength which is proportional to voltage×distance between the electrodes. (For eukaryotic cells, use 0.4 kV, 960 microFarad). Transfer the DNA-cell mixture to the bottom of a cold electroporation cuvette. Place in chilled cuvette chamber slide, and push the slide into the chamber to make contact with the electrodes. Pulse once per sample. The time constant should be between 4–5 milliseconds. Remove the cuvette and immediately add 1 ml of L-broth and resuspend the cells. Transfer the cell suspension to a 1.5 ml polypropylene tube and incubate 37° C. for 1 hour while shaking. Plate cells on agar media with antibiotics, as needed. When used in methods of the invention, an inhibitor or potential inhibitor of restriction activity of an R-M system, such as, but not limited to, 1–5 micrograms of a T3 or T7 OCR Protein for cells having a Type I R-M system, is added to the electrocompetent host cells prior to addition of the unmodified transforming DNA.

Example 3

OCR Protein

OCR Protein, greater than 99% pure by gel electrophoretic analysis, was obtained from EPICENTRE. The protein is prepared generally as described by Atanasiu, C., et al. [Nucleic Acids Res., 29: 3059, 2001]. OCR Protein is provided in a buffer containing 50% glycerol, 100 mM NaCl, 10 mM Tris-HCl (pH7.5), 0.1 mM EDTA, and 1 mM DTT.

Example 4

Transposons and Transposome.sup.TM. Complexes

To construct EZ::TN.sup.TM. <PhoA/R6Kγori/Kan-2> Transposon, a PCR product obtained by amplification of the E. coli phoA gene, encoding amino acid residues 6–450 of mature PhoA, was cloned into the unique XmnI site of a circularized plasmid version of the EZ::TN.sup.TM. <R6Kγ ori/KAN-2> Transposon (EPICENTRE). The circularized transposons are replicated in E. coli hosts expressing the product of the pir gene of R6K, such as E. coli TransforMax.sup.TM. EC100D.sup.TM. pir-116 (EPICENTRE). The transposon was then cloned into the PvuII site of a pUC19-based plasmid to allow amplification of the transposon by PCR using primers flanking the transposon (i.e., pMOD <MCS> Forward and Reverse PCR Primers, EPICENTRE). The amplified transposon was cleaved with BoxI (Fermentas) to release a 3340 basepair transposon. The final construct has an open reading frame (orf) from the first triplet of the transposon encoding a promoter-less, signal peptide-free PhoA, a conditional R6Kγ origin of replication, and the Tn903 kanamycin resistance gene. When the transposon is fused in the correct orientation and reading frame with an exported protein gene, a screenable PhoA phenotype results.

Synaptic complexes (or "Transposome™ complexes") were formed in vitro as described previously [Goryshin, I. Y., et al., Nature Biotechnol., 18: 97–100, 2000; Hoffman, L. M., et al., Genetica, 108: 19–24, 2000]. The DNA concentration of synaptic complexes was between 25–50 ng/microliter. Transposomes were electroporated into electrocompetent cells as described below. Transposon insertion clones were selected on LB plates containing 10 micrograms/ml kanamycin.

Example 5

Plasmids and Fosmids

Plasmid pUC19 was isolated by alkaline lysis following standard purification methods [see Maniatis, T., Fritsch, E. F., and Sambrook, J., Molecular Cloning, A Laboratory Manual, Cold Spring Harbor Laboratory Press, Cold Spring Harbor, N.Y., 1982]. DNA concentration was determined on a Hoefer DyNAQuant Fluorimeter. Fosmids pIB8 and pIB9 were obtained from Mike Fiandt (EPICENTRE) and consisted of approximately 40 kb of unidentified soil microorganism DNA cloned into pEpiFOS.sup.TM.-5 Vector (EPICENTRE), a single-copy, blunt-ended cloning vector.

Example 6

Transformation Efficiencies of pUC19 Plasmid DNA Using Different Strains of Salmonella typhimurium and Escherichia coli The results obtained following electroporation of pUC19 DNA into different strains of S. typhimurium and E. coli are presented in Table 1. As shown, the transformation efficiency of pUC19 in wild type S. typhimurium strain LT2 was about 500-fold lower than in E. coli strain EC100. The EC100 strain contains a chromosomal deletion that removes its type I R-M genes so that it neither modifies nor restricts DNA. pUC19 encodes three recognition sites for the S. thyphimurium StyLTIII R-M system. The inventors reasoned that if the Type I R-M recognition sites on pUC19 were not modified (methylated) so as to protect these sites when the plasmid replicated in E. coli, then Salmonella LT2 was capable of restricting those sites. This is supported by the fact that the efficiency of transformation of pUC19 for a non-restricting S. typhimurium strain, LB5000 [Bullas, L. R. and Ryu, J., J. Bacteriol., 156: 471–474, 1983], was much higher than for S. typhimurium strain LT2, by approximately two orders of magnitude (Table 1). Interestingly, the transformation efficiency of pUC19 for Salmonella strain LB5000 plasmid was at least as high as for the restriction-minus electrocompetent E. coli strain EC100 cells.

Example 7

Effect of OCR Protein on Transformation Efficiency by a Plasmid

The OCR protein of T7 bacteriophage is extremely acidic in character, and closely resembles double-stranded DNA in charge and structure. It is known to act as a molecular decoy and to bind to Type I restriction enzyme complexes in E. coli [Atanasiu, et al., Nucl. Acids Res., 29: 3059–3068, 2001; Walkinshaw, et al., Molec. Cell, 9: 187–194, 2002]. We tested the ability of OCR Protein to be introduced into cells by electroporation and to inhibit the activity of the cell's Type I R-M systems. Thus, one microgram of the OCR Protein was added to the electroporation cuvette along with electrocompetent S. typhimurium strain LT2, and then pUC19 plasmid was added and the cells were electroporated as before. Surprisingly, the transformation efficiency of the pUC19 DNA for the S. typhimurium strain LT2 was approximately one hundred-fold higher in the presence of OCR Protein than in its absence (Table 1).

TABLE 1

Efficiency of Plasmid Transformation in S. typhimurium and E. coli EC100

| Strain | 1 micro-g OCR Protein | cfu/micro-g DNA* |
|---|---|---|
| E. coli EC100 | − | 5–6 × $10^9$ |
| S. typhimurium LT2 | − | 1 × $10^7$ |
| S. typhimurium LT2 | + | 1 × $10^9$ |
| S. typhimurium LB5000 | − | 2 × $10^{10}$ |

*In each case, 100 pg of pUC19 DNA was electroporated

There are many instances of extremely low transformation efficiencies with strains having uncharacterized or active Type I R-M systems. The OCR protein may facilitate transformation of species not currently transformable by electroporation. Cosmids, BACs or fosmids from non-modifying strains of E. coli can be transformed into restricting microorganisms with higher frequency using the OCR protein as decoys for Type I enzymes.

Example 8

Effect of OCR Protein on Transformation Efficiency by an Artificial Transposon in a Transposome™ Synaptic Complex The ability of OCR Protein to increase in vivo transposition efficiency by transposon synaptic complexes was evaluated. The inventors reasoned that if the OCR Protein could overcome the restriction of transposons introduced into the host cells in the form of Transposome complexes, then the in vivo transposition frequency by these Transposomes would also increase. The use of Tn5 and Mu transposon synaptic complexes for in vivo transposition have been described [U.S. Pat. No. 6,294,385; Goryshin, I-Y., et al., Nature Biotechnol., 18: 97–100, 2000; Hoffman, L., et al., Genetica, 108: 19–24, 2000; Lamberg, et al., Appl. Env. Microbiol., 68: 705–712, 2002). Transposomes are stable complexes of hyperactive Tn5 transposase with any DNA having terminal nineteen-basepair inverted repeats (MEs, mosaic ends). Transposomes may be electroporated into many cell types for insertional mutagenesis [Goryshin, et al., Nature Biotechnol., 18: 97–100, 2000]. The transposon EZ::TN<phoA/R6Kγ ori/KAN>, as linear double-stranded DNA, contains six recognition sites (GAGNNNNNNR-TAYG) for the S. typhimurium StyLTIII Type I restriction enzyme [Titherage, et al. Nucl. Acids Res., 29: 4195–4205, 2001]. This transposon was complexed with hyperactive Tn5 transposase to prepare a synaptic complex [Goryshin, et al., Nature Biotechnol., 18: 97–100, 2000; Hoffman, et al., Genetica, 108: 19–24, 2000], and then electroporated into S. typhimurium strain LT2 cells with or without the addition of one microgram of the OCR Protein. As shown in Table 2, the transposition efficiency of S. typhimurium strain LT2 cells by EZ::TN<PhoA/R6Kγori/KAN-2> Transposome was increased by 45-fold in the presence of one microgram of OCR Protein compared to the same cells electroporated without OCR Protein. As also shown in Table 2, when the EZ::TN<phoA/R6Kγ ori/KAN-2> Transposomes were electroporated into non-restricting S. typhimurium strain LB5000 cells, OCR Protein did not affect transposition efficiency, indicating that OCR Protein was acting by inhibiting restriction activity in the S. typhimurium strain LT2 cells.

A similar experiment was also carried out with S. typhimurium strain LT2 cells using the EZ::TN<R6Kγ ori/KAN-2> Transposome, which also contains six StyLTIII Type I restriction sites. In this case, one microgram of the OCR Protein had an even larger effect, increasing in vivo transposition efficiency by 75-fold compared to the same cells in the absence of OCR Protein (Table 2). On the other hand, OCR Protein did not have any effect on transposition efficiency of the non-restricting S. typhimurium strain LB5000 (Table 2).

The amount of OCR Protein used was evaluated for its effects on in vivo transposition efficiency. Thus, a range of OCR Protein quantities was electroporated into S. typhimurium strain LT2 cells along with the EZ::TN<R6Kγ ori/KAN-2> Transposome. Maximal effects on transposition efficiency were found with five micrograms of OCR Protein per 50 microliters of cells (data not shown). However, the electroporation time constant decreased with increasing OCR Protein concentration, and the possibility of arcing increased.

Transposome complexes were also electroporated into Agrobacterium tumefaciens, a bacterium with no detectable Type I R-M system [Wood, et al. Science, 294: 2317–2323, 2001]. OCR Protein (one microgram) did not alter the transposition efficiency of EZ::TN<R6Kγ ori/KAN-2> Transposomes (Table 2), indicating that the effects of OCR Protein may be limited to strains with Type I R-M systems. The addition of OCR Protein did not cause a significant change (neither an increase nor a decrease) in Transposome insertion efficiency in other bacterial species under conditions when there was either no restriction activity in the cell or no sites for the Type I R-M restriction enzyme in the transposon (data not shown).

There is wide variation—approximately three orders of magnitude—in the efficiency of transposition by Transposomes which are electroporated into different host cell types [Goryshin, I. Y., et al., Nature Biotechnol., 18: 97–100, 2000; Hoffman, L., et al., Genetica, 108: 19–24, 2000]. Some of the variation may be due to the degree of electrocompetence of the cells. Restriction of transposon DNA by the host can account for a significant part of the variation. Thus, the inclusion of OCR protein during electroporation of Transposome synaptic complexes increases the efficiency of transposition when transposons contain sites recognized by the Type I R-M activities of the host.

TABLE 2

Effects of OCR on In Vivo Transposition with Transposomes

| Species and Strain | Transposon | 1micro-g OCR Protein | cfu/micro-g DNA |
|---|---|---|---|
| S. typhimurium LT2 | <phoA/R6Ky ori/Kan> | − | 1.6 × $10^3$ |
| S. typhimurium LT2 | " | + | 7.2 × $10^4$ |
| S. typhimurium LB5000 | " | − | 4.4 × $10^5$ |
| S. typhimurium LB5000 | " | + | 4.4 × $10^5$ |
| S. typhimurium LT2 | <R6Kγ ori/Kan-2> | − | 2.4 × $10^4$ |
| S. typhimurium LT2 | " | + | 1.8 × $10^6$ |
| Agrobacterium tumefaciens | " | − | 1.4 × $10^6$ |
| Agrobacterium tumefaciens | " | + | 1.1 × $10^6$ |

Example 9

Effect of OCR Protein on Transformation Efficiency of *Escherichia coli* Strain MG1655 by Fosmid DNA Type I R-M systems are widespread, if not ubiquitous, in bacteria and archaebacteria [Murray, N. E., *Microbiol. Molec. Biol. Rev.* 64: 412–434, 2000; Titherage et al., *Nucl. Acids Res.*, 29: 41954205, 2001], and may pose difficulties with many cross species transformations and transpositions. The EcoKI Type I enzyme complex is associated with the plasma membrane in *E. coli* and the recognition subunit, HsdR, has access to the periplasm [Holubova, et al., *Biochem. Biophys. Res. Commun.* 270: 46–51, 2000].

Electroporation is becoming the method of choice for introduction of DNA into bacterial cells, but in many instances Type I R-M activities reduce transformation efficiency. The present invention shows that OCR Protein can be electroporated into cells, and increase transformation efficiency (as well as transposition efficiency) by unmodified transforming DNA in several species, presumably, by binding to the R-M system and inhibiting restriction activity of the R-M system. The highly negatively charged character of OCR Protein probably allows it to enter the cell during electroporation, perhaps, without limiting the invention, interacting with membrane-bound Type I HsdR Protein on its way into the cell. Since the presence of Type I R-M recognition sites cannot be predicted in unknown sequences of transforming DNA, the inventors used fosmid clones of soil microorganism genomic DNA to assess the value of OCR Protein addition for transformation of replicons containing unknown potential restriction sites. The genomic DNA molecules cloned in the fosmids were approximately 40-kb in length and contained DNA with many NotI restriction sites, indicating a high G+C content. *E. coli* strain MG1655 was chosen for the recipient host strain, because it has EcoKI restriction activity [Blattner, F. R., et al., *Science*, 277: 1453–1462, 1997]. As shown in Table 3, the addition of OCR Protein (one microgram) to transformations of *E. coli* strain MG1655 with either of two fosmids, PIB8 or pIB9, caused an increase in transformation efficiency of between 500- to 1700-fold. Thus, OCR Protein dramatically increased transformation efficiency of fosmid genomic DNA clones containing uncharacterized DNA sequences, when the host expressed Type I restriction activity.

TABLE 3

Effect of OCR on fosmid transformation in MG1655 *E. coli* (EcoKI +)

| Host cell | Fosmid Clone | 1 micro-g OCR Protein | cfu/micro-g DNA |
|---|---|---|---|
| MG 1655 *E. coli* | pIB8 | – | $8 \times 10^2$ |
| " | pIB8 | + | $1.4 \times 10^6$ |
| " | pIB9 | – | $2.3 \times 10^3$ |
| " | pIB9 | + | $1.1 \times 10^6$ |

Example 10

Preparation of a New Host Cell Strain with Improved Transformation Efficiency by in Vivo Insertion of an Artificial Transposon Containing an ocr Gene that is Constitutively Expressed in *E. coli*.

A PCR product comprising the 0.3 ocr gene from bacteriophage T7, having an RNA polymerase promoter that is constitutively expressed in *E. coli*, is end repaired and 5'-phosphorylated using the End-It.sup.TM. DNA End Repair Kit according to the protocols provided in the kit (EPICENTRE), and ligated into the unique XmnI site of a circularized plasmid version of an EZ::TN.sup.TM. <R6Kγ ori/KAN-2> Transposon (EPICENTRE). The resulting plasmid containing the ocr gene in an artificial transposon is replicated in *E. coli* hosts expressing the product of the pir gene of R6K, such as *E. coli* strain TransforMax.sup.TM. EC100D.sup.TM. pir-116 (EPICENTRE). An EZ::TN.sup.TM.  artificial transposon is prepared by PCR amplification using the plasmid as a template and primers flanking the transposon. The resulting linear artificial transposon is used to make a synaptic complex ("Transposome.sup.TM. complex") as described previously [Goryshin, I. Y., et al., *Nature Biotechnol.*, 18: 97–100, 2000; Hoffman, L. M., et al., *Genetica*, 108: 19–24, 2000]. Synaptic complexes can be stored at minus 70.sup.degree. until used for transformation. Electrocompetent *E. coli* strain MG1655 cells are prepared substantially as in Example 1, and then a 50- or 100-microliter suspension of these cells are transformed by electroporation with the EZ::TN Transposome.sup.TM. (having a DNA concentration between 25–50 ng/microliter) substantially as described in Example 2, except that 1–5 micrograms of OCR protein is also added to the cells prior to addition of the synaptic complex and electroporation. The addition of OCR Protein to the electroporation reactions results in an increased efficiency of transposition compared to a control electroporation without OCR protein. Transposon insertion clones are selected on LB plates containing 10 micrograms/ml kanamycin. The resulting kanamycin-resistant insertion clones of *E. coli* strain MG1655 (designated as "*E. coli* strain MG1655/ocr/KAN.sup.R.") express constitutive levels of OCR Protein. When this strain is used to prepare electrocompetent cells and is used as a host cell strain for transformation by unmodified recombinant DNA in plasmids or other vectors, at least about a 10–50-fold higher transformation efficiency is obtained compared to the transformation efficiency obtained using the parent *E. coli* MG1655 strain which lacks the transposon insertion having the expressed ocr gene. Both chemically competent and electrocompetent *E. coli* strain MG1655/KAN.sup.R. cells have improved transformation efficiency with unmodified transforming DNA compared to the strain which lacks an expressed ocr gene.

Example 11

Preparation of a New Host Cell Strain with Improved Transformation Efficiency by in Vivo Insertion of an Artificial Transposon Containing an ardA or ardB Gene that is Constitutively Expressed in *E. coli*.

The experiments described in Example 10 are repeated, except that the gene used to prepare the artificial transposon is an ardA gene. The resulting host strain, designated *E. coli* strain MG1655/ardA/KAN.sup.R, constitutively expresses an ArdA Protein. Both chemically-competent and electrocompetent cells prepared using these strains have improved transformation efficiency by unmodified transforming DNA compared to the corresponding strain which lacks an expressed ard gene.

Example 12

Improvement of Commercially-Important Bacterial Strains

OCR Protein can be used to improve transformation efficiency of *Lactococcus lactis*, or other lactic acid-producing bacteria of commercial importance used as host cells. The protein is added at the time of transformation of the competent host cells with unmodified DNA, such as, but not limited to, unmodified DNA from another strain which is cloned in a plasmid. *Streptococcus thermophilus* is also known to have Type I restriction activities [*Current Microbiol.*, 42: 122–128, 2001], and is an important dairy bacterium. The methods of the invention can also be used to make improved strains by introducing into the genomic DNA of the strain an expressible gene for OCR Protein, ArdA Protein, ArdB Protein, ArdC Protein, or another protein inhibitor of the invention by putting the gene, having a suitable promoter (preferably a conditional promoter, such as an araB promoter) and other characteristics needed for expression in the strain, into a transposon, which in turn, is used to make a synaptic complex which is electroporated into competent cells of the strain so as to bring about transposition into the genome of the strain. When the gene is introduced into the strain using a transposon, the insertion site of the gene in cell DNA is sequenced bi-directionally by using primers complementary to each end of the transposon. Alternatively, the expressible gene for the inhibitor of restriction activity of the strain is introduced into the genome of the strain by transformation of competent cells of the strain with a suicide plasmid containing the gene in expressible form for the strain.

Example 13

Use of Inhibitors of Restriction to Facilitate *Mycoplasma* Research

*Mycoplasma* are the smallest free-living organisms, are widespread in nature, and are involved in many human disease states. They have some of the most complex R-M systems ever discovered, most of which are highly similar to Type I enzymes from enteric bacteria. OCR protein, ArdA Protein, ArdB Protein, ArdC Protein, or other inhibitors of the invention can be used to improve transformation efficiency of *Mycoplasma* species, which can facilitate genetic studies of these organisms.

What is claimed is:

1. A method for improving transformation efficiency of a prokaryotic host cell having a Type I restriction and modification (R-M) system by an unmodified transforming DNA, said method comprising introducing into the prokaryotic host cell an isolated OCR protein, which protein is encoded by a T3 or T7 bacteriophage gene, together with the unmodified transforming DNA.

2. The method of claim 1 wherein the prokaryotic host cell is selected from the group consisting of Eubacteria and Archaebacteria.

3. The method of claim 1 wherein the OCR protein is encoded by the 0.3 ocr gene of bacteriophage T7 or bacteriophage T3.

4. The method of claim 1 wherein the OCR protein and the unmodified transforming DNA are introduced into the prokaryotic host cell by electroporation.

5. The method of claim 1 wherein the unmodified transforming DNA is a polynucleotide comprising recombinant DNA in a vector.

6. The method of claim 1 wherein the unmodified transforming DNA is selected from the group consisting of a transposon and an artificial transposon.

7. The method of claim 1 wherein the unmodified transforming DNA is a polynucleotide selected from the group consisting of a plasmid, a suicide plasmid, a shuttle vector, a cosmid, a fosmid, an oligonucleotide, an amplicon, an episome, a BAC, a YAC, and a replicon.

* * * * *